(12) United States Patent
Echigo et al.

(10) Patent No.: US 9,150,491 B2
(45) Date of Patent: Oct. 6, 2015

(54) BICYCLOHEXANE DERIVATIVE COMPOUND AND MANUFACTURING METHOD OF THE SAME

(75) Inventors: Masatoshi Echigo, Hiratsuka (JP); Dai Oguro, Hiratsuka (JP)

(73) Assignee: Mitsubishi Gas Chemical Company, Inc, Tokyo (JP)

( * ) Notice: Subject to any disclaimer, the term of this patent is extended or adjusted under 35 U.S.C. 154(b) by 398 days.

(21) Appl. No.: 13/522,292

(22) PCT Filed: Jan. 13, 2011

(86) PCT No.: PCT/JP2011/000154
§ 371 (c)(1),
(2), (4) Date: Sep. 19, 2012

(87) PCT Pub. No.: WO2011/086933
PCT Pub. Date: Jul. 21, 2011

(65) Prior Publication Data
US 2013/0030211 A1   Jan. 31, 2013

(30) Foreign Application Priority Data
Jan. 14, 2010   (JP) ................................. 2010-006202

(51) Int. Cl.
| | | |
|---|---|---|
| *C07C 69/54* | (2006.01) | |
| *C07C 43/12* | (2006.01) | |
| *C07C 43/23* | (2006.01) | |
| *C07C 59/72* | (2006.01) | |
| *C07C 69/712* | (2006.01) | |
| *C08F 20/28* | (2006.01) | |
| *C08F 220/28* | (2006.01) | |
| *C08K 5/04* | (2006.01) | |
| *G03F 7/039* | (2006.01) | |

(52) U.S. Cl.
CPC .................. *C07C 69/54* (2013.01); *C07C 43/12* (2013.01); *C07C 43/23* (2013.01); *C07C 59/72* (2013.01); *C07C 69/712* (2013.01); *C08F 20/28* (2013.01); *C08F 220/28* (2013.01); *C08K 5/04* (2013.01); *G03F 7/0392* (2013.01); *G03F 7/0397* (2013.01); *C07C 2101/14* (2013.01)

(58) Field of Classification Search
CPC ........ C07C 43/12; C07C 43/23; C07C 59/72; C07C 69/54; C07C 69/712; C07C 2101/14; C08F 20/28; C08F 220/28; C08K 5/04; G03F 7/0392; G03F 7/0397
USPC .............................. 560/61, 205; 568/664, 720
See application file for complete search history.

(56) References Cited

U.S. PATENT DOCUMENTS

| | | | |
|---|---|---|---|
| 5,102,578 A | 4/1992 | Buchecker | |
| 2008/0008962 A1* | 1/2008 | Watanabe et al. | 430/270.1 |

FOREIGN PATENT DOCUMENTS

| | | |
|---|---|---|
| DE | 4030031 A1 | 3/1992 |
| EP | 0388150 A1 | 9/1990 |
| JP | H2-104548 A | 4/1990 |
| JP | H2-240039 A | 9/1990 |
| JP | H4-039665 A | 2/1992 |
| JP | H06-279341 A | 10/1994 |
| JP | H10-45639 A | 2/1998 |
| JP | H10-319595 A | 12/1998 |
| JP | H11-286465 A | 10/1999 |
| JP | 2000-122295 A | 4/2000 |
| JP | 2003-167346 A | 6/2003 |
| JP | 2003-286215 A | 10/2003 |
| JP | 2007-031402 A | 2/2007 |
| JP | 2009-025684 A | 2/2009 |
| SU | 1816754 A1 | 5/1993 |

OTHER PUBLICATIONS

International Search Report from the International Bureau of WIPO for International Application No. PCT/JP2011/000154 dated Apr. 12, 2011 (4 pages) and an English translation of the same (4 pages).
Office Action dated Oct. 21, 2014, issued in corresponding Japanese Patent Application No. 2011-549943 and the English translation of the same. (4 pages).

* cited by examiner

*Primary Examiner* — Paul A Zucker
*Assistant Examiner* — Mark Luderer
(74) *Attorney, Agent, or Firm* — Fitch Even Tabin & Flannery LLP

(57) ABSTRACT

A bicyclohexane derivative compound useful in the field of photoresist, the field of intermediate of drugs and pesticides, and the like, and a manufacturing method of the same are provided. A bicyclohexane derivative compound represented by the following general formula (II) is provided.

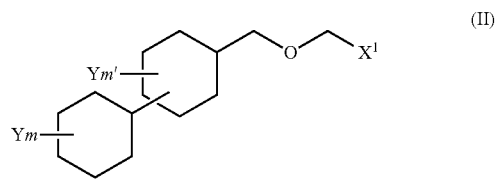

(II)

(In formula (II), Y independently represents an alkyl group of 1 to 10 carbons, a halogen atom, an acyloxy group, an alkoxycarbonyl group or a hydroxyl group, $X^1$ represents a halogen atom, m represents an integer of 0 to 11, and m represents an integer of 0 to 10.).

6 Claims, No Drawings

BICYCLOHEXANE DERIVATIVE COMPOUND AND MANUFACTURING METHOD OF THE SAME

CROSS-REFERENCE TO RELATED APPLICATIONS

This application is a U.S. national phase application filed under 35 U.S.C. §371 of International Application PCT/JP2011/000154, filed on Jan. 13, 2011, designating the United States, which claims priority from Japanese Application 2010-006202, filed Jan. 14, 2010, which are hereby incorporated herein by reference in their entirety.

TECHNICAL FIELD

This invention relates to a novel bicyclohexane derivative compound, a resin and a radiation sensitive composition containing the same as raw material, and a manufacturing method of the same.

RELATED ART

A bicyclohexane structure, a derivative of which shows a unique function, is useful as a photoresist resin, a liquid immersion exposure material and a dry etching resistance improver in the photolithography field, an intermediate of drugs and pesticides, and the like (e.g., JP-A-2003-286215 and JP-A-2009-25684). Also, a protecting group using chloromethylether is useful as a protecting group of a positive type low molecular weight resist and a monomer of an ArF resist resin (JP-A-2007-31402). However, chloromethylether having a bicyclohexane structure has not yet been reported.

Meanwhile, a functional resin composition used in the semiconductor production step requires properties such as changing an irradiation portion into alkali soluble upon light irradiation, etching resistance, substrate adhesion and transparency to light source used in a balanced manner. When the light source uses a short wavelength light source not longer than a KrF excimer laser, a chemical amplification type resist is generally used, and its composition is generally used as a solution containing a functional resin as a main agent and a photo acid generator, and further several kinds of additives. Among them, it is important that a functional resin as a main agent has each of the above properties in a balanced manner, which determines the resist performance.

When the light source uses a short wavelength light source not longer than a KrF excimer laser, a chemical amplification type resist is used, and in that regard, a functional resin as a main agent is generally a polymer having acrylate and the like as a repeating unit. However, it is not used as a single repeating unit. The reason is that a single repeating unit cannot meet all properties such as etching resistance. In practice, a plurality of repeating units each having a functional group for improving each property, more specifically two kinds or more of copolymers are each used in a functional resin. In a KrF excimer laser lithography resist, a hydroxystyrene based resin, and in an ArF excimer laser lithography resist, an acrylic resin having 2-alkyl-2-adamantylmethacrylate as a basic framework have been suggested (see JP-A-H4-39665 and JP-A-H10-319595), and the basic framework is almost determined.

However, miniaturization in the lithography process has been rapidly developed in the recent years, and each light source requires extension to the line width of about one third of the wavelength. Particularly, in ArF excimer laser lithography, due to application of liquid immersion technology, any further miniaturization has been required. Along with that, requirements to the resolution and the line edge roughness have become difficult as the line width has become thin. The causes thereof include the nonuniformity of a functional resin due to great differences in the nature of each repeating unit (see SEMICON JAPAN SEMI Technology Symposium 2002, 3-27).

In order to solve the problem, copolymerization of an existing resin with various acrylate compounds, alternatively changing the structure itself of an existing resin substantially, and the like have been considered. For example, a resist composition containing an adamantane carboxylic acid derivative, which is alkali soluble and etching resistant, has been suggested (see JP-A-2000-122295). Also, as a resist composition having a characteristic such as surface roughness upon etching and small line edge roughness, a copolymer having an acrylate ester derivative containing acrylate represented by 2-(1-adamantyl)-2-methacryloyloxypropane and the like in a basic framework in a main chain has been suggested (see JP-A-2003-167346). However, the actual situation is that it is difficult to sufficiently meet the resolution and the line edge roughness in thinning. From these circumstances, development of a radiation sensitive composition excellent in alkali developability and substrate adhesion, which can achieve improvement in the resolution and the line edge roughness without adversely affecting the basic property of a functional resin composition, has been strongly demanded.

SUMMARY OF THE INVENTION

Objectives to be Achieved by the Invention

The objectives of the invention are (1) to provide (monohalogen substituted methyl)(bicyclohexyl group-containing alkyl)ethers as a novel bicyclohexane derivative compound useful as a modifier and a dry etching resistance improver of a photoresist resin in the photolithography field, an intermediate of drugs and pesticides, other various industrial products and the like, and a manufacturing method of the same, (2) to provide a bicyclohexane derivative compound useful as an optical material such as a crosslinkable resin, an optical fiber, an optical waveguide, an optical disk substrate and a photoresist, and raw material thereof, an intermediate of drugs and pesticides, other various industrial products, and the like, and (3) to provide a functional resin, a radiation sensitive composition and a raw material compound thereof, all excellent in alkali developability and substrate adhesion, which can achieve improvement in the resolution and the line edge roughness without deteriorating the basic physical property of a resist such as pattern shape, dry etching resistance and heat resistance, as a chemical amplification type resist sensitive to far-ultraviolet represented by a KrF excimer laser, an ArF excimer laser, an F2 excimer laser or EUV.

Means for Achieving the Objectives

The inventors have, as a result of devoted examinations to achieve the above objectives, found out that a novel bicyclohexane derivative is a compound appropriate for the above objectives, a resin containing a component obtained from the derivative in a repeating unit and a radiation sensitive composition containing the same are useful as a photoresist, also it is possible to produce them efficiently by a particular process, and therefore the above objectives can be achieved.

More specifically, the invention is as follows.

1. A bicyclohexane derivative compound represented by the following general formula (II).

[Chem. 1]

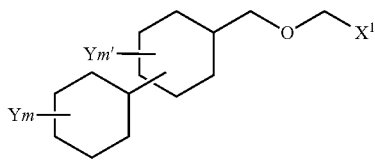
(II)

(In formula (II), Y independently represents an alkyl group of 1 to 10 carbons, a halogen atom, an acyloxy group, an alkoxycarbonyl group or a hydroxyl group, $X^1$ represents a halogen atom, m represents an integer of 0 to 11, and m' represents an integer of 0 to 10.)

2. A bicyclohexane derivative compound represented by the following general formula (VI).

[Chem. 2]

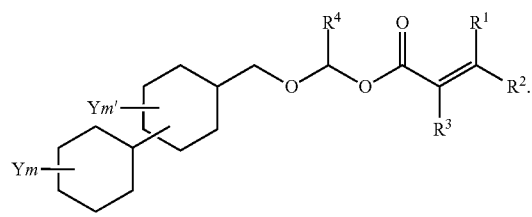
(VI)

(In formula (VI), Y, m and m' are the same as above. $R^1$ to $R^4$ each independently represents a hydrogen atom or an alkyl group of 1 to 3 carbons.)

3. A bicyclohexane derivative compound according to the above item 2, wherein general formula (VI) is the following general formula (VIII) or (IX).

[Chem. 3]

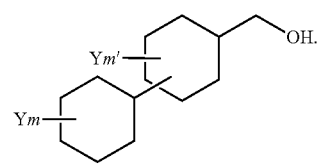
(XIII)

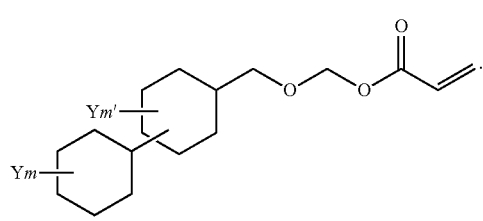
(IX)

4. A bicyclohexane derivative compound represented by the following general formula (III).

[Chem. 4]

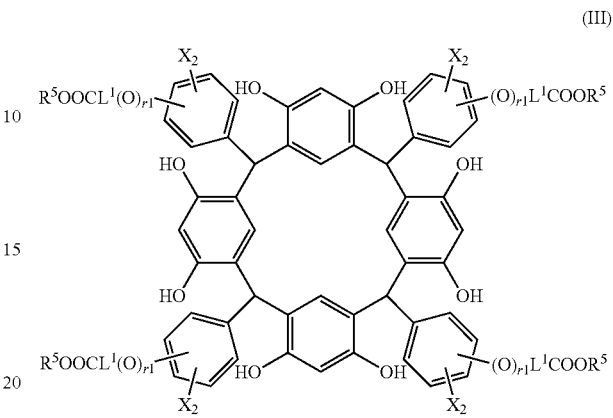
(III)

(In formula (III), $R^5$ is an acid dissociative functional group represented by the following general formula (V), $X^2$ is a hydrogen atom or a halogen atom, $L^1$ is a divalent organic group selected from a single bond, or a linear or branched alkylene group of 1 to 4 carbons, and $r^1$ is 0 or 1.)

[Chem. 5]

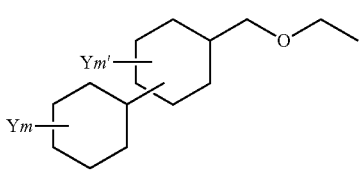
(V)

(In formula (V), Y, m and m' are the same as above.)

5. A bicyclohexane derivative compound represented by the following general formula (III-2).

[Chem. 6]

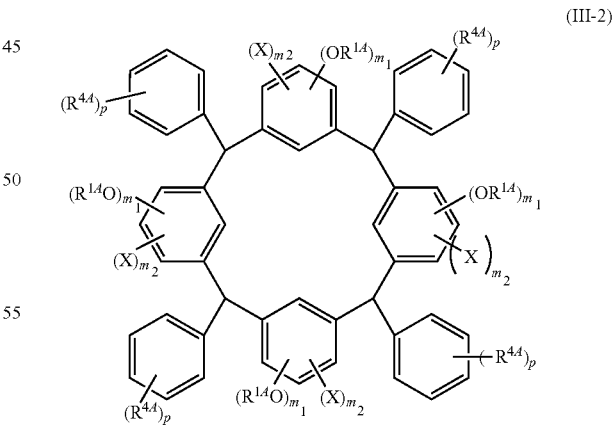
(III-2)

(In formula (III-2), $R^{1A}$ is an acid dissociative functional group represented by the above general formula (V) or a hydrogen atom, at least one of $R^{1A}$ is an acid dissociative functional group represented by the above general formula (V), $R^{4A}$ is a functional group selected from the group consisting of an alkyl group of 1 to 20 carbons, a cycloalkyl group of 3 to 20 carbons, an aryl group of 6 to 20 carbons, an alkoxy group of 1 to 20 carbons, a cyano group, a nitro group, a heterocyclic group, a hydroxyl group, a halogen atom, a carboxyl group and an alkylsilyl group of 1 to 20 carbons, or an acid dissociative functional group selected from the group consisting of a substituted methoxy group of 2 to 20 carbons, a 1-substituted ethoxy group of 3 to 20 carbons, a 1-substituted-n-propoxy group of 4 to 20 carbons, a 1-branched alkyloxy group of 3 to 20 carbons, a silyloxy group of 1 to 20 carbons, an acyloxy group of 2 to 20 carbons, a 1-substituted alkoxyalkyloxy group of 2 to 20 carbons, a cyclic etheroxy group of 2 to 20 carbons, an alkoxycarbonyloxy group of 2 to 20 carbons, an alkoxycarbonylalkyloxy group and a group represented by the following general formula (V-2), X is a hydrogen atom or a halogen atom, $m_1$ is an integer of 1 to 4, p is an integer of 0 to 5, $m_2$ is an integer of 0 to 3, and $m_1+m_2=4$.)

[Chem. 7]

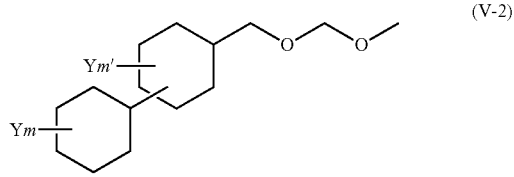

(V-2)

(In formula (V-2), Y, m and m' are the same as above.)

6. A bicyclohexane derivative compound represented by the following general formula (IV).

[Chem. 8]

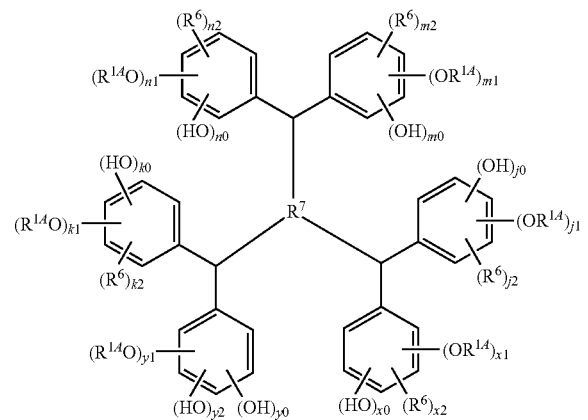

(IV)

(In formula (IV), $R^{14}$ is the same as above, at least one of $R^{14}$ is an acid dissociative functional group represented by the above general formula (V), $R^6$ represents a substituent group selected from the group consisting of a halogen atom, an alkyl group, a cycloalkyl group, an aryl group, an aralkyl group, an alkoxy group, an aryloxy group, an alkenyl group, an acyl group, an alkoxycarbonyl group, an alkyloyloxy group, an aryloyloxy group, a cyano group, and a nitro group;

$R^7$ represents a trivalent substituent group of 6 to 12 carbons having a benzene structure;

k0, j0, m0, n0, x0 and y0 are integers of 0 to 3;
k1, j1, m1, n1, x1 and y1 are integers of 0 to 3;
k2, j2, m2, n2, $X^2$ and y2 are integers of 0 to 4; and
conditions of $1 \le k0+k1+k2 \le 5$, $1 \le j0+j1+j2 \le 5$, $1 \le m0+m1+m2 \le 5$, $1 \le n0+n1+n2 \le 5$, $1 \le x0+x1+x2 \le 5$, $1 \le y0+y1+y2 \le 5$, $1 \le k1+j1+m1+n1+x1+y1 \le 18$, $1 \le k0+k1 \le 3$, $1 \le j0+j1 \le 3$, $1 \le m0+m1 \le 3$, $1 \le n0+n1 \le 3$, $1 \le x0+x1 \le 3$ and $1 \le y0+y1 \le 3$ are met.

However, a plurality of $R^{14}$ and $R^6$ may each be the same or different.)

7. A method of reacting alcohol having a bicyclohexyl group represented by the following general formula (I) with formaldehyde and hydrogen halide gas in the presence of a solvent, to produce the corresponding bicyclohexane derivative compound represented by general formula (II).

[Chem. 9]

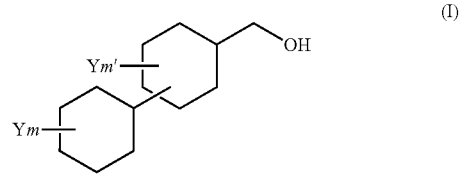

(I)

(In formula (I), Y independently represents an alkyl group of 1 to 10 carbons, a halogen atom, an acyloxy group, an alkoxycarbonyl group or a hydroxyl group, m represents an integer of 0 to 11, and m' represents an integer of 0 to 10.)

[Chem. 10]

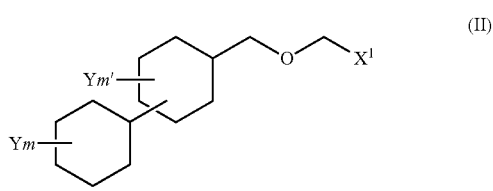

(II)

(In formula (II), Y, m and m' are the same as above. $X^1$ represents a halogen atom.)

8. A manufacturing method of a bicyclohexane derivative compound according to the above item 7, wherein the solvent is an aliphatic hydrocarbon of 5 to 20 carbons.

9. A resin containing a constituent unit represented by the following general formula (X).

[Chem. 11]

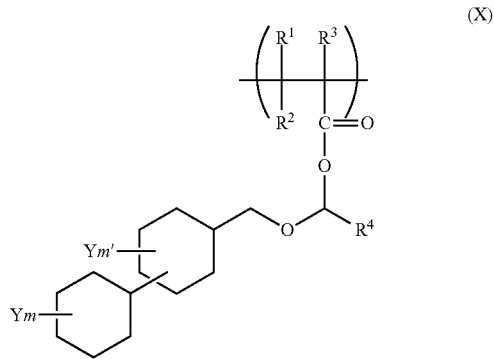

(X)

(In formula (X), $R^1$ to $R^4$, Y, m and m' are the same as above.)

10. A radiation sensitive composition containing a resin according to the above item 9 and a photo acid generator for generating acid by radiation irradiation.

Effects of the Invention

According to the invention,
(1) (monohalogen substituted methyl)(cyclohexylvinyl group-containing alkyl)ethers as a novel bicyclohexane derivative compound useful as a modifier and a dry etching resistance improver of a photoresist resin in the photolithography field, an intermediate of drugs and pesticides, other various industrial products, and the like, and a manufacturing method of the same,
(2) a bicyclohexane derivative compound useful as an optical material such as a crosslinkable resin, an optical fiber, an optical waveguide, an optical disk substrate and a photoresist, and raw material thereof, an intermediate of drugs and pesticides, other various industrial products, and the like, and
(3) a functional resin, a radiation sensitive composition and a raw material compound thereof, all excellent in alkali developability and substrate adhesion, which can achieve improvement in the resolution and the line edge roughness without deteriorating the basic physical property of a resist such as pattern shape, dry etching resistance and heat resistance, as a chemical amplification type resist sensitive to far-ultraviolet represented by a KrF excimer laser, an ArF excimer laser, an F2 excimer laser or EUV, can be provided.

DETAILED DESCRIPTION OF THE PREFERRED EMBODIMENTS

[Bicyclohexane Derivative Compound (II)]

The bicyclohexane derivative compound of the invention is a compound represented by the following general formula (II).

[Chem. 12]

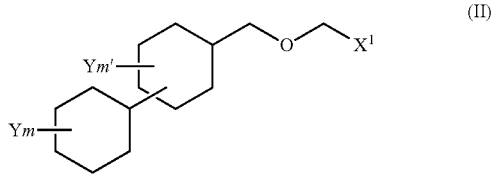

In formula (II), Y independently represents an alkyl group of 1 to 10 carbons, a halogen atom, an acyloxy group, an alkoxycarbonyl group or a hydroxyl group, $X^1$ represents a halogen atom, m represents an integer of 0 to 11, and m' represents an integer of 0 to 10.

The halogen atom for Y can include a fluorine atom, a chlorine atom, a bromine atom and an iodine atom. When Y is an alkyl group of 1 to 10 carbons, the alkyl group may be either linear or branched, and can include a methyl group, an ethyl group, a propyl group, an isopropyl group, various butyl groups, various pentyl groups, various hexyl groups, various heptyl groups, various octyl groups, various nonyl groups and various decyl groups.

Moreover, the acyloxy group is a group represented by $R^{12}$—COO—, and the alkoxycarbonyl group is a group represented by $R^{12}$—OCO—. Here, $R^{12}$ represents a hydrocarbon group of 1 to 10 carbons, which may be either linear, branched or cyclic, the hydrocarbon group includes a linear or branched alkyl group as well as a cyclic hydrocarbon group such as a cycloalkyl group, a phenyl group, an adamantly group and a norbornyl group, and a methyl group, an ethyl group, an isopropyl group and a tert-butyl group are preferable. As Y, an acyloxy group and an alkoxycarbonyl group are preferable, and a tertiary alkoxycarbonyl group is particularly preferable.

The halogen atom for $X^1$ can include a fluorine atom, a chlorine atom, a bromine atom and an iodine atom, normally is a chlorine atom or a bromine atom, and particularly a chlorine atom is preferable.

Also, m represents an integer of 0 to 11, m' represents an integer of 0 to 10, and both are preferable to be integers of 0 to 3.

The bicyclohexane derivative compound of the invention can take either the cis form structure or the trans form structure, but may be either structure or a mixture thereof. When used as a resist component of a radiation sensitive composition, it is preferable to have only one structure of either the cis form or the trans form, since it becomes a pure substance compound and the uniformity of the component within the resist film becomes high. A method for obtaining a cyclic compound having only one structure of either the cis form or the trans form can be conducted by a publicly known method such as separation by column chromatography or preparative liquid chromatography, and optimization of the reaction solvent and the reaction temperature upon production.

[Manufacturing Method of Bicyclohexane Derivative Compound (II)]

The bicyclohexane derivative compound represented by general formula (II) of the invention can be produced by using alcohol having a bicyclohexyl group represented by the following general formula (I) as raw material, and reacting the isomer mixture with formaldehyde and hydrogen halide gas in the presence of a solvent.

[Chem. 13]

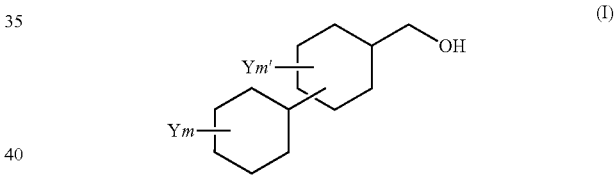

In formula (I), Y, m and m' are the same as above.

For the bicyclohexane derivative compound represented by general formula (II), alcohol having a bicyclohexyl group represented by general formula (I) is used as raw material.

In the manufacturing method of the invention, from the bicyclohexane derivative compound represented by general formula (I), a bicyclohexane derivative compound represented by general formula (II) is obtained.

In the manufacturing method of the invention, the above alcohol having a bicyclohexyl group represented by general formula (I) as raw material is reacted with formaldehyde and dried hydrogen halide (gas) in the presence of a solvent, and a drying agent which is used if needed.

As the above formaldehyde, gaseous formaldehyde, paraformaldehyde, trioxane or the like is used. The amount of formaldehyde is normally 1 to 5 mol per 1 mol of raw material alcohol.

The hydrogen halide gas is preferable to be dried. A method of supplying it from a commercially available tank or a method of supplying hydrogen halide gas generated by reacting sodium halide with concentrated sulfuric acid can be adopted. The amount of hydrogen halide is normally 1 to 20 mol per 1 mol of raw material alcohol.

Moreover, the above drying agent may not be necessary, but when it is used, a general drying agent should be used.

Specifically, it includes an anhydrous inorganic salt such as anhydrous magnesium sulfate, anhydrous iron chloride and anhydrous aluminum chloride; calcium chloride, molecular sieves, diphosphorus pentoxide, sodium perchlorate, active alumina, silica gel, calcium hydride, lithium aluminum hydride, and the like. The amount of the drying agent is normally 0.5 to 5 mol per 1 mol of raw material alcohol.

The solvent used in the manufacturing method of the invention specifically includes a solvent based on aliphatic hydrocarbon of 5 to 20 carbons such as n-hexane and n-heptane, an ether based solvent such as diethyl ether and dibutyl ether, and a halogen based hydrocarbon solvent such as dichloromethane and carbon tetrachloride, a solvent based on aliphatic hydrocarbon of 5 to 20 carbons is preferable, and particularly n-hexane and n-heptane are preferable. Also, the solubility of a solvent to water is preferable to be not more than 5% by mass, since production of a byproduct during the reaction can be limited.

Moreover, the reaction temperature is, when the boiling point of a solvent under the reaction pressure is T° C., desirable to be within a range from (T-70)° C. to T° C. By adjusting it within the range, the production amount of the above byproduct can be limited.

The reaction pressure is, in absolute pressure, normally 0.01 to 10 MPa, and preferably normal pressure to 1 MPa. The reaction time is normally 1 minute to 24 hours, and preferably 30 minutes to 5 hours.

For purification of an objective reaction product, distillation, crystallization, column separation and the like can be adopted, and the purification method may be selected according to the nature of the product and the kind of byproduct.

[Bicyclohexane Derivative Compounds (III), (III-2) and (IV)]

From the bicyclohexane derivative compound represented by general formula (II), a bicyclohexane derivative compound represented by the following general formula (III), (III-2) or (IV) can be derived by reacting with, for example, various calixresorcinarenes, various polynuclear polyphenols and the like under basic conditions such as KOH and NaOH. More specifically, the compound represented by general formula (II) is useful as a positive type resist material, which can be used in KrF excimer laser, electron beam (EB) or extreme ultraviolet (EUV) exposure technology, or raw material of an inhibitable protecting group against an alkali aqueous solution such as an additive.

[Chem. 14]

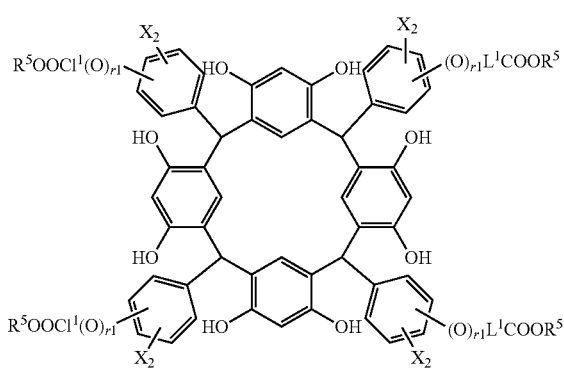

(III)

In formula (III), $R^5$ is an acid dissociative functional group represented by the following general formula (V), $X^2$ is a hydrogen atom or a halogen atom, $L^1$ is a divalent organic group selected from a single bond, or a linear or branched alkylene group of 1 to 4 carbons, and $r^1$ is 0 or 1.

[Chem. 15]

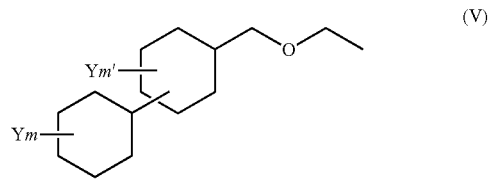

(V)

(In formula (V), m and m' are the same as above.)

The halogen atom for $X^2$ can include a fluorine atom, a chlorine atom, a bromine atom and an iodine atom, normally is a chlorine atom or a bromine atom, and particularly a chlorine atom is preferable. As $X^2$, especially from the perspective of low outgassing property and economic efficiency, a hydrogen atom and a chlorine atom are preferable. Among alkylene groups of 1 to 4 carbons for $L^1$, from the perspective of solvent solubility and film forming property, propylene, sec-butylene and tert-butylene are preferable.

[Chem. 16]

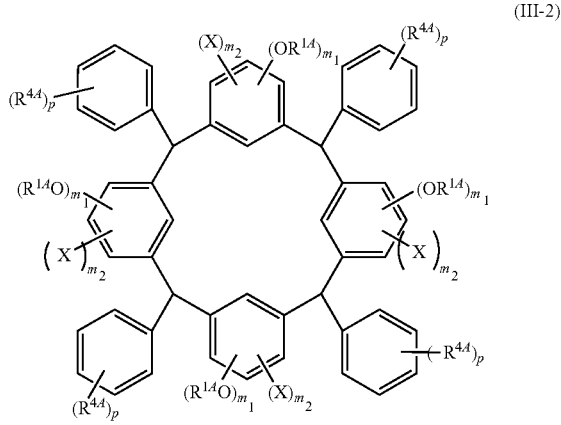

(III-2)

In formula (III-2), $R^{1A}$ is an acid dissociative functional group represented by the above general formula (V) or a hydrogen atom, at least one of $R^{1A}$ is an acid dissociative functional group represented by the above general formula (V), $R^{4A}$ is a functional group selected from the group consisting of an alkyl group of 1 to 20 carbons, a cycloalkyl group of 3 to 20 carbons, an aryl group of 6 to 20 carbons, an alkoxy group of 1 to 20 carbons, a cyano group, a nitro group, a heterocyclic group, a hydroxyl group, a halogen atom, a carboxyl group and an alkylsilyl group of 1 to 20 carbons, or an acid dissociative functional group selected from the group consisting of a substituted methoxy group of 2 to 20 carbons, a 1-substituted ethoxy group of 3 to 20 carbons, a 1-substituted-n-propoxy group of 4 to 20 carbons, a 1-branched alkyloxy group of 3 to 20 carbons, a silyloxy group of 1 to 20 carbons, an acyloxy group of 2 to 20 carbons, a 1-substituted alkoxyalkyloxy group of 2 to 20 carbons, a cyclic etheroxy group of 2 to 20 carbons, an alkoxycarbonyloxy group of 2 to 20 carbons, an alkoxycarbonylalkyloxy group and a group represented by the following general formula (V-2), X is a hydrogen atom or a halogen atom, $m_1$ is an integer of 1 to 4, p is an integer of 0 to 5, $m_2$ is an integer of 0 to 3, and $m_1+m_2=4$.

[Chem. 17]

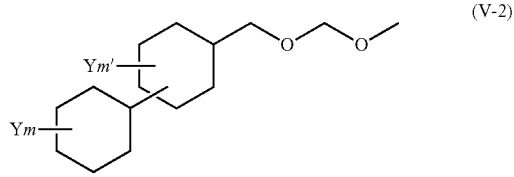

(V-2)

(In formula (V-2), Y, m and m' are the same as above.)

[Chem. 18]

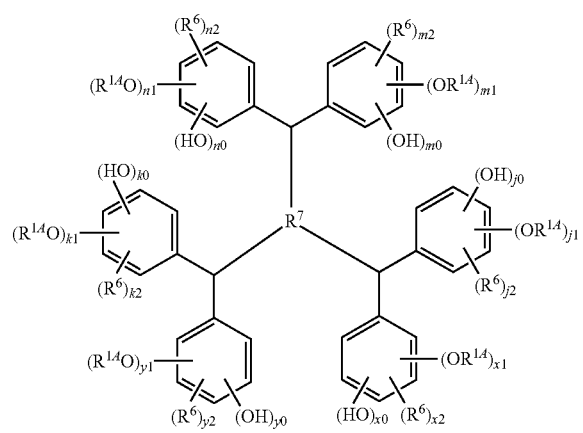

(IV)

In formula (IV), $R^{1A}$ is the same as above, at least one of $R^{1A}$ is an acid dissociative functional group represented by the above general formula (V), $R^6$ represents a substituent group selected from the group consisting of a halogen atom, an alkyl group, a cycloalkyl group, an aryl group, an aralkyl group, an alkoxy group, an aryloxy group, an alkenyl group, an acyl group, an alkoxycarbonyl group, an alkyloyloxy group, an aryloyloxy group, a cyano group and a nitro group;

$R^7$ represents a trivalent substituent group of 6 to 12 carbons having a benzene structure;

k0, j0, m0, n0, x0 and y0 are integers of 0 to 3;
k1, j1, m1, n1, x1 and y1 are integers of 0 to 3;
k2, j2, m2, n2, x2 and y2 are integers of 0 to 4; and
conditions of $1 \leq k0+k1+k2 \leq 5$, $1 \leq j0+j1+j2 \leq 5$, $1 \leq m0+m1+m2 \leq 5$, $1 \leq n0+n1+n2 \leq 5$, $1 \leq x0+x1+x2 \leq 5$, $1 \leq y0+y1+y2 \leq 5$, $1 \leq k1+j1+m1+n1+x1+y1 \leq 18$, $1 \leq k0+k1 \leq 3$, $1 \leq j0+j1 \leq 3$, $1 \leq m0+m1 \leq 3$, $1 \leq n0+n1 \leq 3$, $1 \leq x0+x1 \leq 3$ and $1 \leq y0+y1 \leq 3$ are met.

However, a plurality of $R^{1A}$ and $R^6$ may each be the same or different. From the perspective of production, a combination of k0+k1=1, j0+j1=1, m0+m1=1, n0+n1=1, x0+x1=1 and y0+y1=1 is particularly preferable.

The cyclohexyl portion of the bicyclohexane derivative compound of the invention can take either the cis form structure or the trans form structure, but may be either structure or a mixture thereof. When used as a resist component of a radiation sensitive composition, it is preferable to have only one structure of either the cis form or the trans form, since it becomes a pure substance compound and the uniformity of the component within the resist film becomes high. A method for obtaining a cyclic compound having only one structure of either the cis form or the trans form can be conducted by a publicly known method such as separation by column chromatography or preparative liquid chromatography, and optimization of the reaction solvent and the reaction temperature upon production.

[Bicyclohexane Derivative Compound (VI)]

The bicyclohexane derivative compound (VI) of the invention is a compound represented by the following general formula (VI).

[Chem. 19]

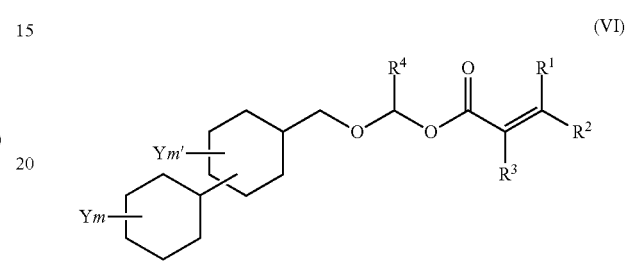

(VI)

In formula (VI), Y, m and m' are the same as above. $R^1$ to $R^4$ each independently represents a hydrogen atom or an alkyl group of 1 to 3 carbons. The alkyl group of 1 to 3 carbons may be either linear or branched, and includes a methyl group, an ethyl group, a propyl group, and an isopropyl group. It is preferable that $R^1$ to $R^4$ are hydrogen atoms or methyl groups, and it is more preferable that $R^1$, $R^2$ and $R^3$ are hydrogen atoms and $R^4$ is a methyl group.

Moreover, the bicyclohexane derivative compound represented by general formula (VI) is preferable to be a compound represented by the following general formula (VIII) or general formula (IX). When the bicyclohexane derivative compound is a compound represented by the following general formula (VIII) or general formula (IX), it has characteristics of being excellent in productivity, and also in various resist performances upon being used as a radiation sensitive composition.

[Chem. 20]

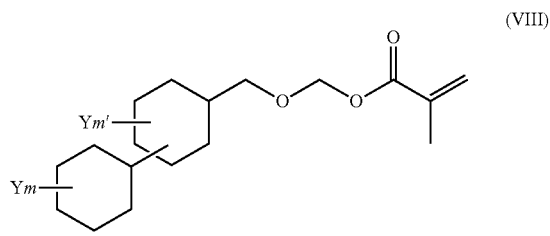

(VIII)

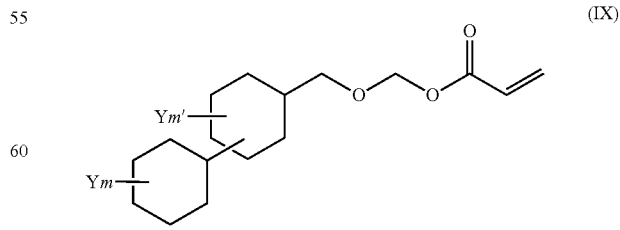

(IX)

The bicyclohexane derivative compound of the invention can take either the cis form structure or the trans form structure, but may be either structure or a mixture thereof. When used as a resist component of a radiation sensitive composition, it is preferable to have only one structure of either the cis form or the trans form, since it becomes a pure substance compound and the uniformity of the component within the resist film becomes high. A method for obtaining a cyclic compound having only one structure of either the cis form or the trans form can be conducted by a publicly known method such as separation by column chromatography or preparative liquid chromatography, and optimization of the reaction solvent and the reaction temperature upon production.

[Manufacturing Method of Bicyclohexane Derivative Compound (VI)]

The bicyclohexane derivative compound represented by general formula (VI) in the invention can be produced by reacting a raw material compound represented by the following general formula (XII) with an acrylic compound such as methacrylic acid and acrylic acid in the presence of a base compound.

[Chem. 21]

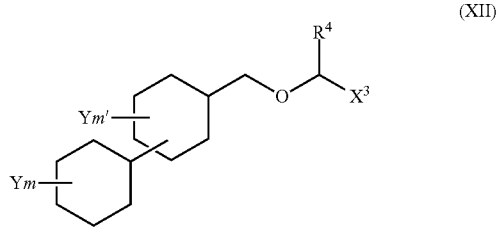

(XII)

In formula (XII), $R^4$, Y, m and m' are the same as above, $X^3$ represents a halogen atom. The halogen atom can include a fluorine atom, a chlorine atom, a bromine atom and an iodine atom, normally is a chlorine atom or a bromine atom, and particularly a chlorine atom is preferable.

The compound represented by general formula (XII) is, for example, obtained by reacting alcohol represented by the following general formula (XIII) with formaldehyde (paraformaldehyde or trioxane) and dried hydrogen halide (gas) in the presence of a hydrocarbon based solvent such as hexane, and a drying agent which is used if needed.

[Chem. 22]

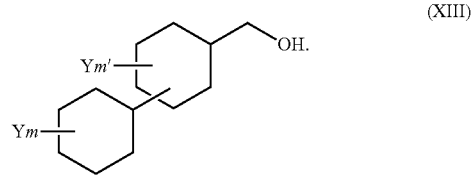

(XIII)

In formula (XIII), Y, m and m' are the same as above.

<<Acrylic Compound>>

Specific examples of the above acrylic compound include acid compounds such as acrylic acid, methacrylic acid, 2-fluoroacrylic acid, trifluoroacrylic acid and 2-(trifluoromethyl)acrylic acid, acrylic acid halides such as acrylic acid chloride, methacrylic acid chloride, 2-fluoroacrylic acid chloride, trifluoroacrylic acid chloride and 2-(trifluoromethyl) acrylic acid chloride, acrylate esters such as methyl acrylate, ethyl acrylate, t-butyl acrylate, methyl methacrylate, ethyl methacrylate, t-butyl methacrylate, methyl trifluoroacrylate, ethyl trifluoroacrylate, isopropyl trifluoroacrylate, t-butyl trifluoroacrylate, methyl pentafluoromethacrylate, ethyl pentafluoromethacrylate, isopropyl pentafluoromethacrylate, t-butyl pentafluoromethacrylate, methyl 2-fluoroacrylate, ethyl 2-fluoroacrylate, isopropyl 2-fluoroacrylate, t-butyl 2-fluoroacrylate, methyl 2-(trifluoromethyl)acrylate, ethyl 2-(trifluoromethyl)acrylate, isopropyl 2-(trifluoromethyl) acrylate and t-butyl 2-(trifluoromethyl)acrylate, acrylates such as sodium acrylate, sodium methacrylate, sodium 2-fluoroacrylate, sodium trifluoroacrylate and sodium 2-(trifluoromethyl)acrylate, and acrylic anhydrides such as acrylic anhydride, methacrylic anhydride, perfluoroacrylic anhydride, perfluoromethacrylic anhydride, 2,2'-difluoroacrylic anhydride, 2-fluoroacrylic anhydride and 2-trifluoromethylacrylic anhydride. As the acrylic compound, acrylic acid, methacrylic acid, methyl acrylate or methyl methacrylate is normally used, and particularly acrylic acid or methacrylic acid is preferably used. The amount used is 1 to 100 equivalents (the required acryloyloxy group content is 1 equivalent) based on the raw material compound represented by general formula (XIII), preferably 1 to 10 equivalents. The yield decreases with less than that, and it is not economical with more than that.

<<Base Compound>>

As the above base compound to be added, an amine compound as an organic base is preferable. Examples of the amine compound include nitrogen-containing heterocyclic compounds including amines such as methylamine, dimethylamine, trimethylamine, ethylamine, diethylamine, triethylamine, n-propylamine, di-n-propylamine, diisopropylamine, tri-n-propylamine, n-butylamine, di-n-butylamine, diisobutylamine, tri-n-butylamine, diphenylamine, 1,5-diazabicyclo[4.3.0]nonane-5,1,5-diazabicyclo[5.4.0]undecene-5 and diazabicyclo[2.2.2]octane, anilines such as aniline, methylaniline, bromoaniline, nitroaniline and aminobenzoic acid which are organic amines likewise, pyridines such as dimethylaminopyridine, pyrroles, quinolones, piperidines and the like, and particularly triethylamine, which is highly effective, is preferable. Metal alkoxides such as sodium methoxide and lithium methoxide, quaternary ammonium hydroxides such as tetramethylammonium hydroxide and trimethyl-n-propylammonium hydroxide, sulfate, nitrate, chloride and the like of amines such as ethylammonium sulfate, trimethylammonium nitrate and anilinium chloride, an inorganic base such as sodium hydrogen carbonate, and a Grignard reagent such as ethylmagnesium bromide may be present in a reaction solution.

The used amount of these base compounds to be added is preferable to be not more than 10 equivalents based on the raw material compound represented by general formula (XII). There is no supplemental effect with even more than that. A method for adding a based compound is not particularly specified. It may have previously been added before an acrylic compound is added or may be added after an acrylic compound is added, but normally is desirable to be added by dropping simultaneously with an acrylic compound. In that regard, it is desirable that the reaction temperature is controlled so as not to abnormally rise, since the progress of a side reaction can be inhibited.

<<Other Production Conditions Etc.>>

As a solvent, one with high solubility of raw material and objective substance is desirable. As such, a halogen compound such as dichloromethane, chloroform and 1,2-dichloroethane, an ether compound such as tetrahydrofuran, diethylether and methyl t-butylether, a hydrocarbon compound such as benzene and hexane, and the like are included, and particularly a hydrocarbon based solvent such as hexane and heptane is preferable.

The reaction temperature is −70 to 200° C., preferably −50 to 80° C. The reaction speed decreases when it is lower than −70° C., and the reaction control is liable to become difficult or the yield is liable to decrease as the side reaction progresses when it is higher than 200° C.

After the reaction terminates, excessive acrylic compounds, and an additive such as acid and base are removed by washing a reaction solution with water. In this regard, an appropriate inorganic salt such as sodium chloride and sodium hydrogen carbonate may be included in washing water. Also, unreacted acrylic compounds are removed by alkali washing. For the alkali washing, a sodium hydroxide aqueous solution, a potassium hydroxide aqueous solution, a sodium carbonate aqueous solution, a sodium hydrogen carbonate aqueous solution, ammonia water and the like are included, but an alkali component to be used is not particularly specified. Moreover, for removing metal impurities, acid washing may be conducted. For the acid washing, an inorganic acid such as a hydrochloric acid aqueous solution, a sulfuric acid aqueous solution and a phosphoric acid aqueous solution, and an organic acid such as an oxalic acid aqueous solution are included. Also, upon washing, according to the physical property of a bicyclohexane derivative compound represented by general formula (VI), an organic solvent may be added to a reaction solution. The organic solvent to be added may be the same as the reaction or may be different, but normally it is desirable to use a less polar solvent which is easily separated from water.

Each reaction step in the invention can be conducted under normal pressure, reduced pressure or increased pressure. Also, the reaction can be conducted by a method in common use such as batch type, semi-batch type and continuous type. In each step, each derivative may be isolated, or may be used in the next step while remaining in a solution state without isolation. After the reaction terminates, it can be easily separated and purified by a method in common use, for example a separation means such as filtration, concentration, distillation, extraction, crystallization, recrystallization, column chromatography and activated carbon purification, or a separation means in combination thereof. When distillation is conducted, it is preferable to add a polymerization inhibitor having a boiling point higher than the boiling point of an objective product.

[Resin]

The resin of the invention contains a component represented by the following general formula (X) as a constituent unit, and particularly is preferable to contain a component represented by the following general formula (XI) as a constituent unit.

[Chem. 23]

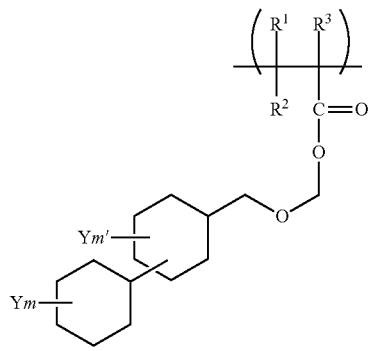

(X)

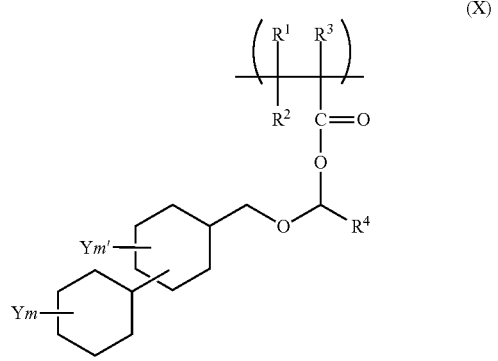

(XI)

In formulae (X) and (XI), $R^1$ to $R^4$, Y, m and m' are the same as above.

The resin of the invention can be produced by homopolymerization or copolymerization from a bicyclohexane derivative compound (monomer) represented by general formula (VI). In polymerization, generally, a polymerization reaction is conducted by dissolving a monomer in a solvent, adding a catalyst and heating or cooling. The polymerization reaction depends on polymerization conditions such as the kind of initiator, the initiation method such as heat or light, the temperature, the pressure, the concentration, the solvent and the additive. In polymerization of the functional resin of the invention, radical polymerization using a radical generator such as azoisobutyronitrile, ion polymerization using a catalyst such as alkyllithium, and the like are commonly used. The method can be conducted by the law of the art.

In the invention, raw material of a copolymer with the bicyclohexane derivative represented by general formula (VI) includes the followings: an adamantly acrylate derivative such as 2-methyl-2-adamantyl(meth)acrylate, 2-ethyl-2-adamantyl(meth)acrylate, 2-(meth)acryloyloxy-2-(1-adamantyl)propane, 2-(meth)acryloyloxy-2-(1-adamantyl)butane and 3-(meth)acryloyloxy-3-(1-adamantyl)pentane, a hydroxystyrene derivative such as hydroxystyrene, α-methylstyrene, 4-t-butoxystyrene, 4-t-butoxycarbonyloxystyrene, 4-t-butoxycarbonylmethyloxystyrene and 4-(2-t-butoxycarbonylethyloxy)styrene, t-butyl(meth)acrylate, isobornyl (meth)acrylate, tricyclodecanyl(meth)acrylate, β-(meth)acryloyloxy γ-butyrolactone, β-(meth)acryloyloxy β-methyl-γ-butyrolactone, α-(meth)acryloyloxy γ-butyrolactone, α-(meth)acryloyloxy α-methyl-γ-butyrolactone, α-(meth)acryloyloxy γ,γ-dimethyl-γ-butyrolactone, 5-(meth)acryloyloxy 3-oxatricyclo[4.2.1.0⁴,⁸]nonane-2-one(=9-(meth)acryloyloxy 2-oxatricyclo[4.2.1.0⁴,⁸]nonane-3-one), 6-(meth)acryloyloxy 3-oxatricyclo[4.3.1.1⁴,⁸]undecane-2-one and the like. Raw material of a copolymer can be present alone or in combination of two kinds or more.

The polystyrene converted weight average molecular weight (hereinafter, referred to as "Mw") as measured by gel permeation chromatography (GPC) of the resin of the invention is preferably 1,000 to 150,000, more preferably 3,000 to 100,000. Also, the ratio between Mw of the resin and the polystyrene converted number average molecular weight (hereinafter, referred to as "Mn") as measured by gel permeation chromatography (GPC) (Mw/Mn) is normally 1 to 10, preferably 1 to 5. The resin of the invention can be used alone or in a mixture of two kinds or more.

The cyclohexyl portion of the resin of the invention can take either the cis form structure or the trans form structure, but may be either structure or a mixture thereof. When used as a resist component of a radiation sensitive composition, it is preferable to have only one structure of either the cis form or the trans form, since it becomes a pure substance compound and the uniformity of the component within the resist film becomes high. A method for obtaining a cyclic compound having only one structure of either the cis form or the trans form can be conducted by a publicly known method such as separation by column chromatography or preparative liquid chromatography, and optimization of the reaction solvent and the reaction temperature upon production.

[Radiation Sensitive Composition]

The radiation sensitive composition of the invention is a composition containing the above resin and/or compound and a photo acid generator for generating acid by radiation irradiation.

The photo acid generator can be arbitrarily selected from ones usable as an acid generator of a chemical amplification type resist composition, according to exposure light wavelength, in consideration of the thickness range of a resist coat and the optical absorption coefficient of itself. The photo acid generator can be used alone or in combination of two kinds or more. The used amount of the acid generator is preferably 0.1 to 20 parts by mass per 100 parts by mass of resin, more preferably 0.5 to 15 parts by mass.

In the far-ultraviolet region, a usable photo acid generator includes, for example, an onium salt compound, a sulfonimide compound, a sulfone compound, a sulfonate ester compound, a quinonediazide compound, a diazomethane compound, and the like. Particularly, to the laser wavelength of 193 nm of an ArF excimer laser, an onium salt compound such as a sulfonium salt, an iodonium salt, a phosphonium salt, a diazonium salt and a pyridinium salt is preferable.

To the laser wavelength of 193 nm of an ArF excimer laser, a preferably usable photo acid generator can specifically include triphenylsulfonium triflate, triphenylsulfonium hexafluoroantimonate, triphenylsulfonium naphthalenesulfonate, (hydroxyphenyl)benzylmethylsulfonium toluenesulfonate, diphenyliodonium triflate, diphenyliodonium pyrenesulfonate, diphenyliodonium dodecylbenzensulfonate, diphenyliodonium hexafluoroantimonate, and the like.

An acid diffusion controller having a function of controlling a diffusion phenomenon within a resist coat of an acid generated from a photo acid generator by exposure and inhibiting an unpreferable chemical reaction in an unexposed region can be compounded.

As an acid diffusion controller, a nitrogen-containing organic compound, wherein the basicity does not change by exposure and heat process in the step of forming a resist pattern, is preferable. Such a nitrogen-containing organic compound can include, for example, monoalkylamines such as n-hexylamine, n-heptylamine and n-octylamine; dialkylamines such as di-n-butylamine; trialkylamines such as triethylamine; aromatic amines such as aniline, N,N-dimethylaniline, 2-methylaniline, 3-methylaniline, 4-methylaniline, 4-nitroaniline and diphenylamine; an amine compound such as ethylenediamine, an amide compound such as formamide, N,N-dimethylformamide, N,N-dimethylacetamide and N-methylpyrolidone, a urea compound such as urea, imidazoles such as imidazole and benzimidazole, pyridines such as pyridine and 4-methylpyridine, 1,4-diazabicyclo[2.2.2]octane, and the like. The compounding amount of the acid diffusion controller is normally not more than 15 parts by weight per 100 parts by weight of resin, preferably 0.001 to 10 parts by weight, more preferably 0.005 to 5 parts by weight.

The radiation sensitive composition of the invention can further contain a solvent.

A commonly used solvent can include, for example, linear ketones such as 2-pentanone and 2-hexanone; cyclic ketones such as cyclopentanone and cyclohexanone, propylene glycol monoalkyl acetates such as propylene glycol monomethyl ether acetate and propylene glycol monoethyl ether acetate, ethylene glycol monoalkyl ether acetates such as ethylene glycol monomethyl ether acetate and ethylene glycol monoethyl ether acetate, propylene glycol monoalkyl ethers such as propylene glycol monomethyl ether and propylene glycol monoethyl ether; ethylene glycol monoalkyl ethers such as ethylene glycol monomethyl ether and ethylene glycol monoethyl ether, diethylene glycol alkyl ethers such as diethylene glycol dimethyl ether and diethylene glycol diethyl ether, esters such as ethyl acetate and ethyl lactate, alcohols such as cyclohexanol and 1-octanol, ethylene carbonate, γ-butyrolactone, and the like. These solvents can be used alone or in a mixture of two kinds or more.

Moreover, the radiation sensitive composition of the invention can also contains, if needed, various additive components which are also used in a conventional chemical amplification type resist composition, for example, various additives such as a surfactant, a quencher, a sensitizer, a halation inhibitor, a storage stabilizer and an antifoamer. A preferable sensitizer can include, for example, carbozoles, benzophenones, rose bengals, anthracenes, and the like.

A usable surfactant can include, for example, nonionic surfactants such as polyoxyethylene lauryl ether and polyethylene glycol dilaurate, as well as surfactants commercially available under the following trade names, MEGAFAC F173 (made by DIC), L-70001 (made by Shin-Etsu Chemical), EFTOP EF301, EF303, EF352 (made by Jemco), Fluorad FC430, FC431 (made by Sumitomo 3M), AsahiGuard AG710, Surflon S-382, SC101, SC102, SC103, SC104, SC105, SC106 (made by Asahi Glass), KP341 (made by Shin-Etsu Chemical), Polyflow No. 75, No. 95 (made by Kyoeisha Chemical), and the like.

In order to form a resist pattern from the radiation sensitive composition of the invention, a radiation sensitive composition solution prepared as described above is applied on a substrate such as silicon wafer, metal, plastic, glass and ceramic, for example, by an appropriate application means such as spin coater, dip coater and roller coater to form a resist coat, possibly heat treated at a temperature of about 50° C. to 200° C. in advance, and then exposed via a predetermined mask pattern. The thickness of a coat is for example 0.1 to 20 μm, preferably about 0.3 to 2 μm. For exposure, light beams with various wavelengths such as ultraviolet and X-ray can be used, and for example, as a light source, far-ultraviolet such as an F2 excimer laser (157 nm wavelength), an ArF excimer laser (193 nm wavelength) and a KrF excimer laser (248 nm wavelength), extreme ultraviolet (13 nm wavelength), X-ray, an electron beam, and the like are arbitrarily selected and used. Also, the exposure condition such as the exposure amount is arbitrarily selected according to the compounding composition of the above resin and/or compound, the kind of each additive and the like.

In the invention, in order to stably form a highly accurate fine pattern, after exposure, it is preferable to conduct heat treatment at a temperature of 50 to 200° C. for 30 seconds or more. In this case, variation in sensitivity due to the kind of substrate is liable to be increased. Thereafter, a predetermined resist pattern is formed by developing under conditions of normally at 10 to 50° C. for 10 to 200 seconds, preferably at 20 to 25° C. for 15 to 90 seconds by an alkaline developing solution.

As the above alkaline developing solution, for example, an alkaline aqueous solution having an alkaline compound such as alkali metal hydroxide, ammonia water, alkylamines, alkanolamines, heterocyclic amines, tetraalkylammonium hydroxides, choline, 1,8-diazabicyclo-[5.4.0]-7-undecene and 1,5-diazabicyclo-[4.3.0]-5-nonene dissolved to be a concentration of normally 1 to 10% by weight, preferably 1 to 3% by weight is used. Also, to a developing solution comprising the above alkaline aqueous solution, a water soluble organic solvent and a surfactant can also be added arbitrarily.

EXAMPLES

Below, the invention will be described in further detail by Examples and Comparative Examples, but the invention should not be in any waylimited by these Examples.

Synthesis Example 1A Synthesis of BCHCME

To a 5000 ml autoclave, 910 g of 2-propanol (IPA, Wako Pure Chemical Industries, special grade), 364 g of biphenyl aldehyde made by Mitsubishi Gas Chemical (2.0 mol), 7.3 g of 5% Ru/Al$_2$O$_3$ (made by N. E. CHEMCAT) and 10 MPa of hydrogen were charged, and stirred at 150° C. for 8 h. After cooling, a catalyst was filtered under an inert gas atmosphere. After a solvent was removed, distillation was conducted under reduced pressure to obtain bicyclohexyl methanol (BCHM) (80% yield, 99% purity).

The chemical shift values (δ ppm, TMS standard) of $^1$H-NMR of the resulting product in a heavy chloroform solvent were 0.7 to 2.0 (m, 21H), 2.8 (s, 1H), and 3.5 (m, 2H). From 3.5, it is thought that two doublets are confirmed in an integration ratio of 3:2 and the ratio between the cis form and the trans form is 3:2.

[Chem. 24]

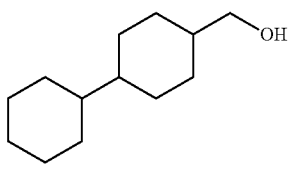

(BCHM)

Subsequently, in a four necked flask (1000 ml) equipped with a dropping funnel, a Dimroth condenser tube, a thermometer and a stirring blade, which is sufficiently dried and substituted with nitrogen, to a solution comprising BCHM (39.27 g) and 132 ml of n-hexane, 18.0 g of trioxane was added under a nitrogen gas stream. Thereafter, under ice cooling, it was stirred while blowing hydrogen chloride gas for 4 hours. After the reaction terminated, blowing of hydrogen chloride gas was stopped, it was allowed to cool back to room temperature, an insoluble layer was separated by a separatory funnel, anhydrous sodium sulfate was added to an n-hexane layer, it was stirred at room temperature, and then filtration treatment was conducted. A solvent was removed from the resulting filtrate, and then single distillation was conducted under reduced pressure to obtain 41.0 g of BCHCME as an objective product represented by the following chemical formula.

The chemical shift values (δ ppm, TMS standard) of $^1$H-NMR of the resulting product in a heavy chloroform solvent were 0.7 to 2.0 (m, 21H), 3.5 (m, 2H), and 5.4 (d, 2H).

[Chem. 25]

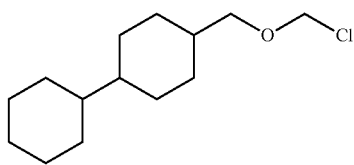

(BCHCME)

Synthesis Example 2A Synthesis of BCHCME

Synthesis was conducted similarly to Synthesis Example 1A, except that n-hexane was substituted with methylene chloride. As a result, an objective product was obtained with a yield of 35.0 g.

Synthesis Example 1B Synthesis of EtP-3EtO4HBA

In a four necked flask (1000 ml) equipped with a dropping funnel, a Dimroth condenser tube, a thermometer and a stirring blade, which is sufficiently dried and substituted with nitrogen, to a solution comprising 3-ethoxy-4-hydroxybenzaldehyde (25.2 g/100 mmol), potassium carbonate (13.8 g/100 mmol) and 200 ml of THF, 100 ml of dimethylformamide solution of 19.5 g (100 mmol) of ethyl α-bromobutyrate was dropped under a nitrogen gas stream. The reaction solution was stirred for 24 hours under reflux.

After the reaction terminated, a solvent was removed, and the resulting solid was purified by column chromatography using a mixed solvent of hexane/ethyl acetate=1/3. 13.0 g of EtP-3EtO4HBA having a phenolic hydroxyl group substituted with an ethoxycarbonylpropyl group was obtained. The chemical shift values (δ ppm, TMS standard) of $^1$H-NMR of the resulting product in a heavy DMSO solvent were 1.1 to 1.3 (m, 9H), 2.1 (m, 2H), 3.2 to 3.3 (m, 2H), 4.2 (m, 2H), 4.7 (t, 1H), 7.1 to 7.9 (m, 3H), and 9.9 (s, 1H).

[Chem. 26]

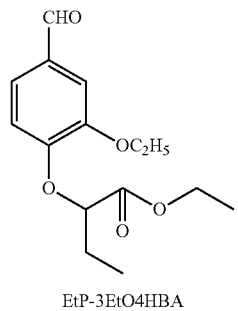

EtP-3EtO4HBA

Synthesis Example 2B Synthesis of EtE-3MeO4HBA

It was synthesized similarly to Synthesis Example 1B, except that 3-ethoxy-4-hydroxybenzaldehyde (o-ethyl vanillin) was substituted with 3-methoxy-4-hydroxybenzaldehyde (o-ethyl vanillin) and ethyl α-bromobutyrate was substituted with ethyl α-bromopropionate. As a result, 10.0 g of EtE-3MeO4HBA having a phenolic hydroxyl group substituted with an ethoxycarbonylethyl group was obtained. The chemical shift values (δ ppm, TMS standard) of $^1$H-NMR of the resulting product in a heavy DMSO solvent were 1.1 to 1.3 (m, 6H), 3.8 (m, 3H), 4.2 (m, 2H), 4.9 (s, 1H), 7.1 to 7.6 (m, 3H), and 9.9 (s, 1H).

[Chem. 27]

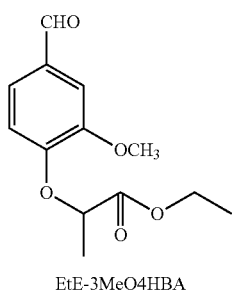

EtE-3MeO4HBA

Synthesis Example 1C Synthesis of CR-1

To a four necked flask (1000 ml) equipped with a dropping funnel, a Dimroth condenser tube, a thermometer and a stirring blade, which is sufficiently dried and substituted with nitrogen, resorcinol (5.5 g, 50 mmol) made by Kanto Chemical, EtP-3EtO4HBA (12.6 g, 50 mmol) obtained in Synthesis Example 1B and ethanol (330 ml) were charged to prepare an ethanol solution. Next, after dropping 75 ml of concentrated hydrochloric acid (35%) by a dropping funnel at room temperature over 60 minutes, it was stirred at 80° C. for 48 hours. After the reaction terminated, it was allowed to cool back to room temperature, a sodium hydroxide aqueous solution was added, and it was stirred for 24 hours. Thereafter, this solution was transferred to a reparatory funnel, diethyl ether was added to separate, the water layer thereof was taken out, neutralization was conducted by hydrochloric acid, and a precipitated solid was filtered and vacuum dried, and as a result, 11.5 g of an objective product CR-1 represented by the following chemical formula was obtained.

The result of LC-MS analysis of this compound showed the molecular weight of 1377. Also, the chemical shift values (δ ppm, TMS standard) of $^1$H-NMR in a heavy DMSO solvent were 1.0 to 1.2 (m, 24H), 2.1 to 2.2 (m, 8H), 3.2 to 3.3 (m, 8H), 4.6 (s, 4H), 5.2 to 5.5 (t, 4H), 6.0 to 6.8 (m, 20H), 8.6 (brs, 8H), and 12.9 (brs, 4H).

[Chem. 28]

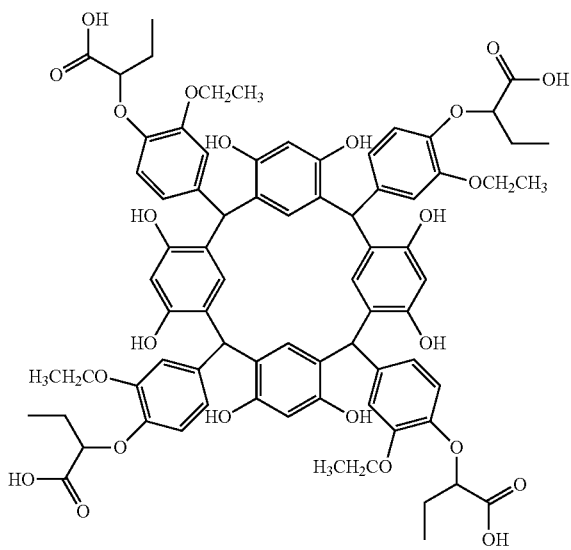

CR-1

Synthesis Example 2C Synthesis of CR-2

10.3 g of an objective product CR-2 represented by the following chemical formula was obtained by synthesizing similarly to Synthesis Example 1C, except that EtP-3EtO4HBA was substituted with EtE-3MeO4HBA.

The result of LC-MS analysis of this compound showed the molecular weight of the objective product of 1264. Also, the chemical shift values (δ ppm, TMS standard) of $^1$H-NMR in a heavy DMSO solvent were 1.0 to 1.2 (m, 12H), 3.8 (m, 12H), 4.6 (s, 4H), 5.2 to 5.5 (t, 4H), 6.0 to 6.8 (m, 20H), 8.6 (brs, 8H), and 12.9 (brs, 4H).

[Chem. 29]

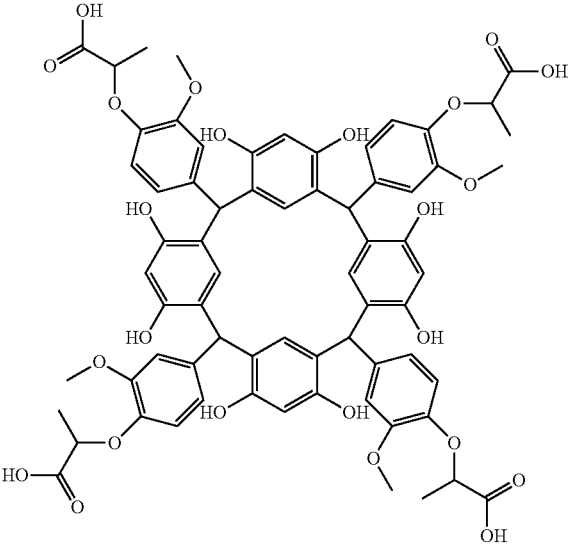

CR-2

Synthesis Example 1D Synthesis of BCHP-CR-1

In a four necked flask (1000 ml) equipped with a dropping funnel, a Dimroth condenser tube, a thermometer and a stirring blade, which is sufficiently dried and substituted with nitrogen, to a solution comprising CR-1 (13.8 g, 10 mmol) synthesized in Synthesis Example 1C, 13.8 g of potassium carbonate and THF (330 ml), 100 ml of THF solution of BCHCME (9.76 g, 40 mmol) synthesized in Synthesis Example 1A was charged under a nitrogen gas stream to prepare a tetrahydrofuran solution. Next, it was stirred at room temperature for 6 hours. After the reaction terminated, a reaction solution was concentrated and purified by column chromatography, a column developing solvent was distilled, an obtained solid was filtered and vacuum dried, and 11.0 g of an objective product BCHP-CR-1 represented by the following chemical formula was obtained.

The result of LC-MS analysis of this compound showed the molecular weight of the objective product of 2209. Also, the chemical shift values (δ ppm, TMS standard) of $^1$H-NMR in a heavy DMSO solvent were 0.7 to 2.2 (m, 116H), 3.2 to 3.3 (m, 8H), 3.5 (m, 8H), 4.6 (s, 4H), 5.2 to 5.5 (m, 12H), 6.0 to 6.8 (m, 20H), and 8.6 (brs, 8H).

[Chem. 30]

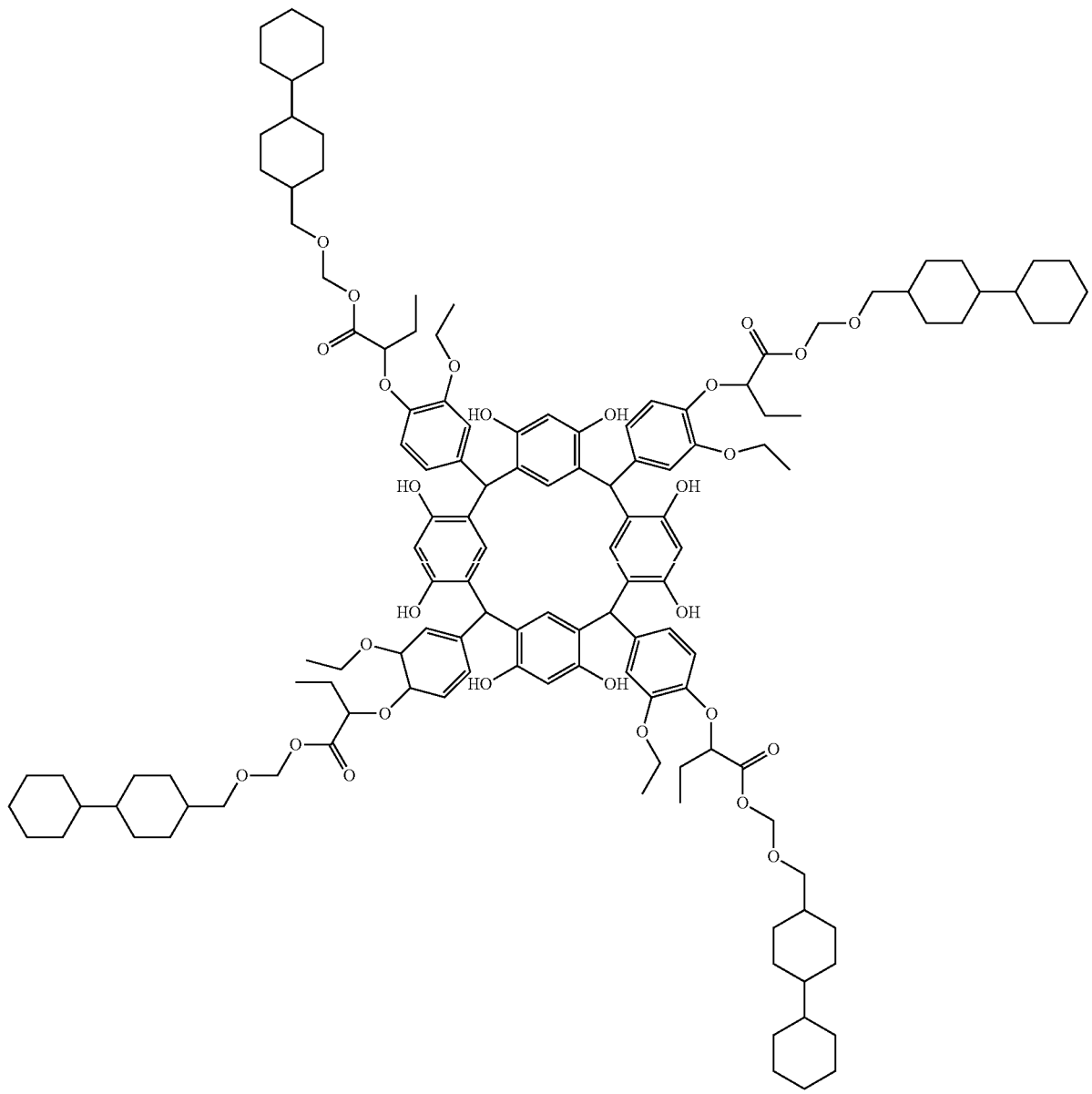

BCHP-CR-1

Synthesis Example 2D Synthesis of BCHP-CR-2

It was synthesized similarly to Synthesis Example 1D, except that CR-1 was substituted with CR-2. As a result, 10.5 g of an objective product BCHP-CR-2 represented by the following chemical formula was obtained.

The result of LC-MS analysis of this compound showed the molecular weight of the objective product of 2097. Also, the chemical shift values (δ ppm, TMS standard) of $^1$H-NMR in a heavy DMSO solvent were 0.7 to 2.0 (m, 96H), 3.5 (m, 8H), 3.8 (m, 12H), 4.6 (s, 4H), 5.2 to 5.5 (m, 12H), 6.0 to 6.8 (m, 20H), and 8.6 (brs, 8H).

[Chem. 31]

BCHP-CR-2

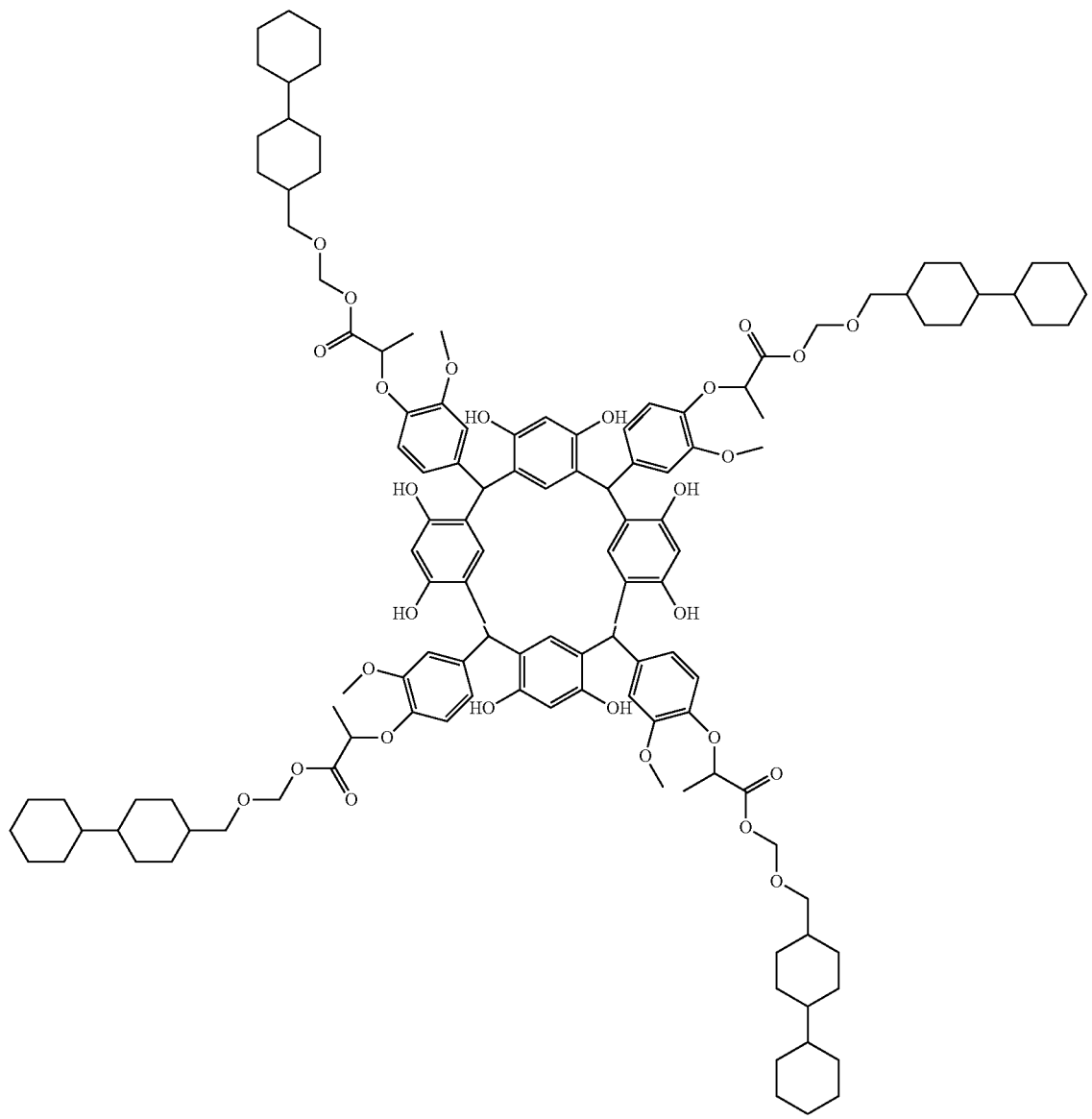

Synthesis Example 3C Synthesis of CR-3

To a four necked flask (1000 ml) equipped with a dropping funnel, a Dimroth condenser tube, a thermometer and a stirring blade, which is sufficiently dried and substituted with nitrogen, resorcinol (22 g, 0.2 mol) made by Kanto Chemical, 4-isopropylbenzaldehyde (29.6 g 0.2 mol) and a dehydrated ethanol (200 ml) were charged under a nitrogen gas stream to prepare an ethanol solution. This solution was heated to 85° C. by a mantle heater while stirring. Next, after dropping 75 ml of concentrated hydrochloric acid (35%) by a dropping funnel over 30 minutes, it was stirred continuously at 85° C. for 3 hours. After the reaction terminated, it was stood to cool to reach room temperature, and then cooled in an ice bath. After having stood still for 1 hour, a pale yellow objective crude crystal was produced, and filtered. The crude crystal was washed twice with 500 ml of methanol, filtered, and vacuum dried to obtain an objective product CR-3 (45.6 g, 95% yield) represented by the following chemical formula.

The result of LC-MS analysis of this compound showed the molecular weight of the objective product of 960. Also, the chemical shift values (δ ppm, TMS standard) of $^1$H-NMR in a heavy dimethyl sulfoxide solvent were 1.1 to 1.2 (m, 24H), 2.6 to 2.7 (m, 4H), 5.5 (s, 4H), 6.0 to 6.8 (m, 24H), and 8.4 to 8.5 (d, 8H).

[Chem. 32]

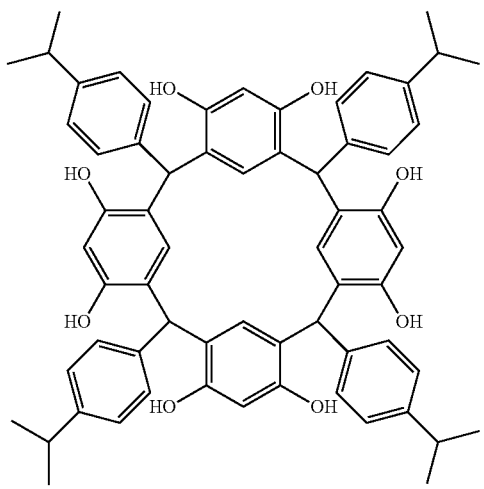

CR-3

Synthesis Example 4C Synthesis of CR-4

To an autoclave (made of SUS316L) equipped with an electromagnetic stirring apparatus, having a capacity of 500 ml, and which can control the temperature, 74.3 g (3.71 mol) of anhydrous HF and 50.5 g (0.744 mol) of $BF_3$ were charged, the content was stirred, and the pressure was increased to 2 MPa by carbon monoxide while maintaining the solution temperature at −30° C. Thereafter, while maintaining the pressure at 2 MPa and the solution temperature at −30° C., raw material having 57.0 g (0.248 mol) of 4-cyclohexylbenzene and 50.0 g of n-heptane mixed was supplied and kept for 1 hour, then the content was collected in ice, diluted with benzene, an oil layer obtained by the neutralization treatment was analyzed by gas chromatography, and the obtained reaction performance was that the 4-cyclohexylbenzene inversion rate was 100% and the 4-cyclohexylbenzaldehyde selection rate was 97.3%. As a result of isolating an objective component by simple distillation and analyzing with GC-MS, 4-cyclohexylbenzaldehyde (hereinafter, represented as CHBAL) as an objective product was obtained. The molecular weight was 188.

Also, the chemical shift values (δ ppm, TMS standard) of $^1$H-NMR in a heavy chloroform solvent were 1.0 to 1.6 (m, 10H), 2.55 (m, 1H), 7.36 (d, 2H), 7.8 (d, 2H), and 10.0 (s, 1H).

Subsequently, to a four necked flask (1000 ml) equipped with a dropping funnel, a Dimroth condenser tube, a thermometer and a stirring blade, which is sufficiently dried and substituted with nitrogen, resorcinol (22 g, 0.2 mol) made by Kanto Chemical, CHBAL (46.0 g, 0.2 mol) and a dehydrated ethanol (200 ml) were charged under a nitrogen gas stream to prepare an ethanol solution. This solution was heated to 85° C. by a mantle heater while stirring. Next, after dropping 75 ml of concentrated hydrochloric acid (35%) by a dropping funnel over 30 minutes, it was stirred continuously at 85° C. for 3 hours. After the reaction terminated, it was stood to cool to reach room temperature, and then cooled in an ice bath.

After having stood still for 1 hour, a pale yellow objective crude crystal was produced, and filtered. The crude crystal was washed twice with 500 ml of methanol, filtered, and vacuum dried to obtain an objective product CR-4 (50 g, 91% yield) represented by the following chemical formula.

The result of LC-MS analysis of this compound showed the molecular weight of the objective product of 1121. Also, the chemical shift values (δ ppm, TMS standard) of $^1$H-NMR in a heavy chloroform solvent were 0.8 to 1.9 (m, 40H), 3.2 (m, 4H), 5.5 to 5.6 (d, 4H), 6.0 to 6.8 (m, 24H), and 8.4 to 8.5 (m, 8H).

[Chem. 33]

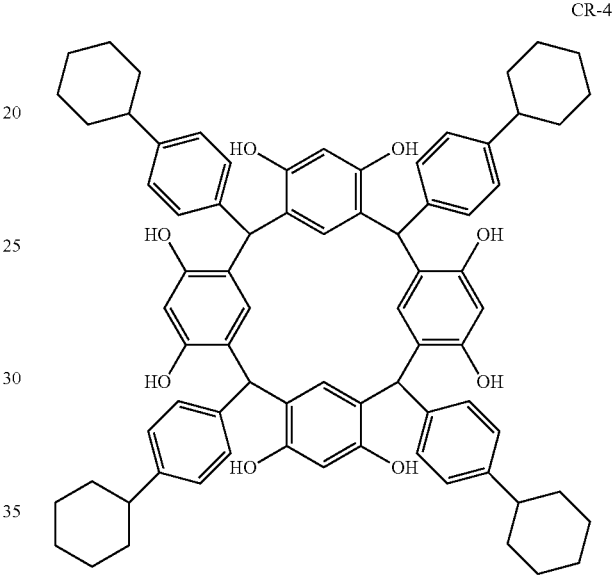

CR-4

Synthesis Example 3D Synthesis of BCH50CR-3

In a four necked flask (1000 ml) equipped with a dropping funnel, a Dimroth condenser tube, a thermometer and a stirring blade, which is sufficiently dried and substituted with nitrogen, to a solution comprising 9.6 g (10 mmol) of CR-3 synthesized in Synthesis Example 3C, 2.0 g (20 mmol) of triethylamine and 500 ml of N-methyl-2-pyrolidone, BCH-CME (9.76 g, 40 mmol) synthesized in Synthesis Example 1A was dropped under a nitrogen gas stream. The reaction solution was stirred at room temperature for 6 hours. After the reaction terminated, a solvent was removed, and the resulting solid was purified by column chromatography using a mixed solvent of hexane/ethyl acetate=1/3. 16.3 g of BCH50CR-3 having 50 mol % of phenolic hydroxyl groups substituted with bicyclohexyl methoxymethyl groups was obtained.

The chemical shift values (δ ppm, TMS standard) of $^1$H-NMR of the resulting product in a heavy dimethyl sulfoxide solvent were 0.7 to 2.0 (m, 108H), 2.6 to 2.7 (m, 4H), 3.5 (m, 8H), 5.4 (d, 8H), 5.5 (s, 4H), 6.0 to 6.8 (m, 24H), and 8.4 to 8.5 (d, 4H).

[Chem. 34]

BCH50CR-3

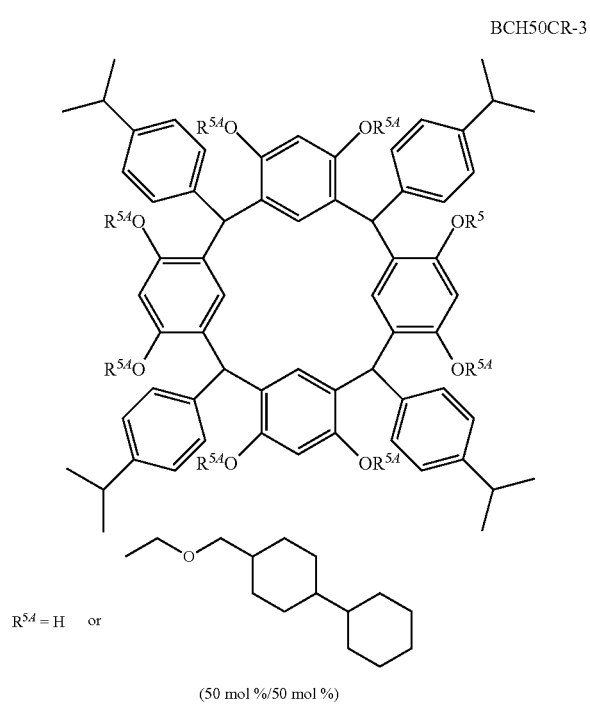

$R^{54}$ = H or

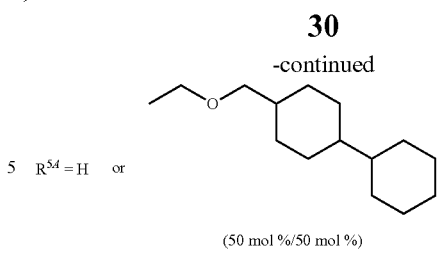

(50 mol %/50 mol %)

Synthesis Example 4D Synthesis of BCH50CR-4

It was synthesized similarly to Synthesis Example 3D, except that CR-3 was substituted with 11.2 g (10 mmol) of CR-4 synthesized in Synthesis Example 4C. As a result, 13.0 g of BCH50CR-4 having 50 mol % of phenolic hydroxyl groups substituted with tricyclodecanyl methoxymethyl groups was obtained. The chemical shift values (δ ppm, TMS standard) of $^1$H-NMR of the resulting product in a heavy dimethyl sulfoxide solvent were 0.7 to 2.0 (m, 124H), 3.2 (m, 4H), 3.5 (m, 8H), 5.4 to 5.6 (m, 12H), 6.0 to 6.8 (m, 24H), and 8.4 to 8.5 (m, 8H).

[Chem. 35]

BCH50CR-4

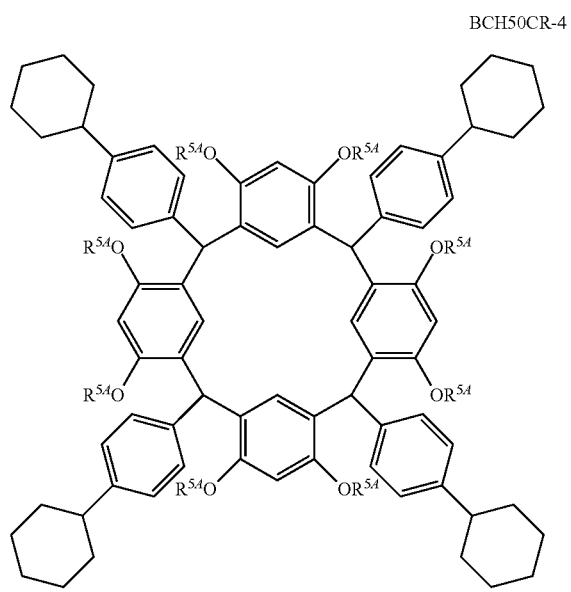

Synthesis Example 1E Synthesis of Tetrakis(2,3,6-trimethylphenol)-1,3,5-benzene Tricarbaldehyde 327.9 g (2.4 mol) of 2,3,6-trimethylphenol (made by Kanto Chemical) and 16.2 g (0.1 mol) of 1,3,5-benzene tricarbaldehyde (synthesized according to Chem. Ber., 1954, 87, 54) were mixed and heated to about 80° C. to dissolve. To this, 0.2 ml of sulfuric acid (made by Kanto Chemical) and 1.6 ml of 3-mercaptopropionic acid (made by Kanto Chemical) were added, and reacted while stirring. After the inversion rate was confirmed to reach 100% by liquid chromatography, 100 ml of toluene (made by Kanto Chemical) was added. A solid precipitated by cooling was filtered under reduced pressure, stirred and washed in warm water at 60° C., and purified by silica gel chromatography to obtain an objective product (XIV) represented in the following chemical formula (XIV).

The structure of the compound was confirmed by elemental analysis and $^1$H-NMR measurement (400 MHz, d-DMSO, internal standard TMS). The results are shown in Table 1 and Table 2.

[Chem. 36]

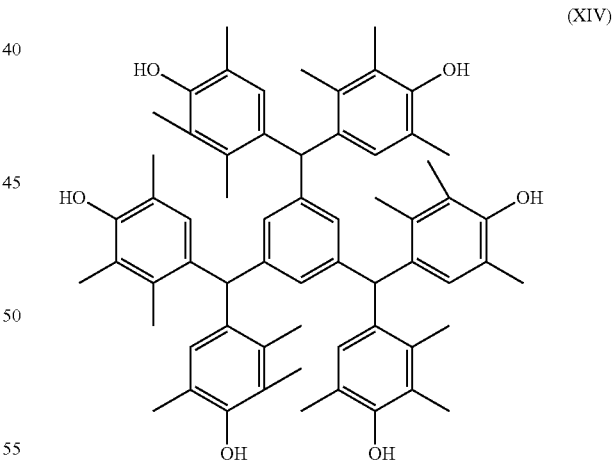

(XIV)

TABLE 1

| Elemental Analysis of Compound (XIV) | | | | | | | | |
|---|---|---|---|---|---|---|---|---|
| Rational Formula | | | Molecular | Calculated Value | | | Observed Value | |
| C | H | O | Weight | C | H | O | C | H |
| 63 | 72 | 6 | 924 | 81.78 | 7.84 | 10.38 | 71.8 | 7.7 |

TABLE 2

| $^1$H-NMR of Compound (XIV) |
| --- |
| $^1$H-NMR |
| 7.8 (6H, —OH), 6.0 to 6.4 (9H, PhH), 5.3 (3H, —CH—), 1.8 to 2.1 (54H, Ph—CH$_3$) |

Synthesis Example 2E

To a solution having 5 ml of N-methyl-2-pyrolidone added to 0.6 g (0.9 mmol) of tetrakis(2,3,6-trimethylphenol)-1,3,5-benzene tricarbaldehyde, BCHCME (0.66 g, 2.7 mmol) synthesized by the above method and 0.18 g of triethylamine were dropped slowly, and stirred at 80° C. for 3 hours. As the reaction solution was added to a large amount of water and reprecipitation was repeated, white powder was obtained. This was dried under reduced pressure to obtain 0.5 g of the objective mixture (XV) represented by the following chemical formula (XV).

The structure of the mixture was confirmed by $^1$H-NMR measurement (400 MHz, d-DMSO, internal standard TMS).

[Chem. 37]

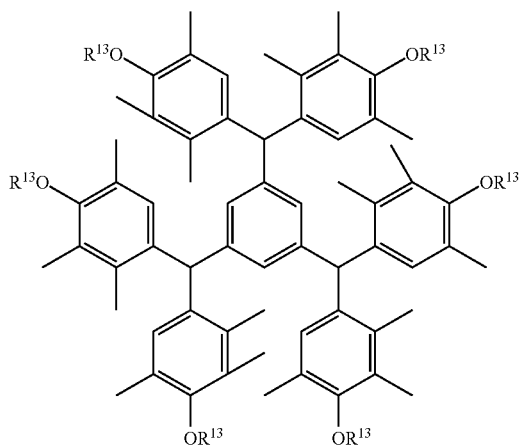

(XV)

In chemical formula (XV), R$^{13}$ is an acid dissociative functional group represented by the following chemical formula or a hydrogen atom, and the ratio is 50 mol %/50 mol %.

[Chem. 38]

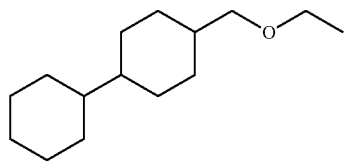

Synthesis Example 1F Synthesis of BCHMMM

To a 200 ml four necked flask, 3.80 g of methacrylic acid (MQ 250 ppm added product) made by Mitsubishi Gas Chemical and 80 ml of toluene were charged, and 4.84 g of triethylamine was dropped under cooling and a nitrogen atmosphere. Next, 7.90 g of BCHCME synthesized similarly to Synthesis Example 1A was dropped, and stirred at room temperature for 3 hours. The reaction solution was washed with 50 ml of distilled water, and then washed with 50 ml of 10% NaCl aqueous solution. A drying treatment was conducted with anhydrous MgSO$_4$, after filtration, 200 ppm of N-nitrosophenyl hydroxylamine aluminum salt was added, and then it was distilled under reduced pressure to obtain BCHMMM represented by the following chemical formula with 98% purity and 98% yield.

The chemical shift values (δ ppm, TMS standard) of $^1$H-NMR of the resulting product in a heavy chloroform solvent were 1.0 to 2.3 (m, 24H), 3.3 to 3.6 (m, 2H), 5.3 to 5.6 (m, 2H), 5.6 (s, 1H), and 6.2 (s, 1H).

[Chem. 39]

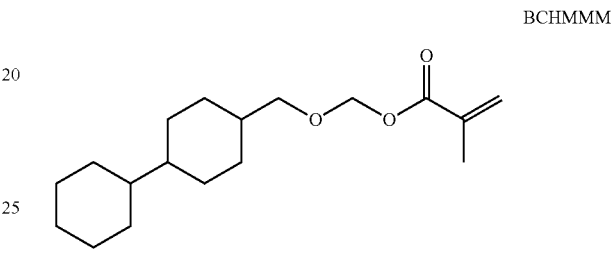

BCHMMM

Synthesis Example 2F Synthesis of BCHMMA

It was synthesized similarly to Synthesis Example 1E, except that methacrylic acid was substituted with acrylic acid (MQ 250 ppm added product) made by Mitsubishi Gas Chemical. As a result, the objective product TCDMMA presented by the following chemical formula was obtained with 98% purity and 98% yield.

The chemical shift values (δ ppm, TMS standard) of $^1$H-NMR of the resulting product in a heavy chloroform solvent were 1.0 to 2.3 (m, 21H), 3.3 to 3.6 (m, 2H), 5.3 to 5.6 (m, 2H), 5.6 (s, 1H), 6.1 (m, 1H), and 6.2 (s, 1H).

[Chem. 40]

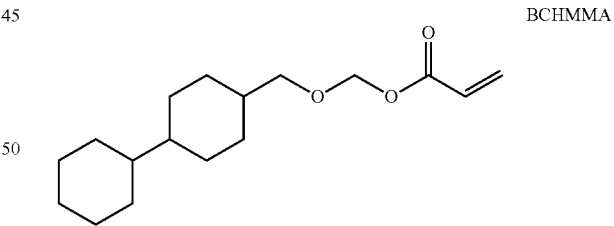

BCHMMA

Synthesis Example 1G Synthesis of Resin 3.0 g of BCHMMM, 2.0 g of γ-butyrolactone methacrylate ester and 1.5 g of hydroxyadamantyl methacrylate ester were dissolved in 45 mL of tetrahydrofuran, and 0.20 g of azobisisobutyronitrile was added. After refluxing for 12 hours, the reaction solution was dropped to 2 l of n-heptane. A precipitated resin was filtered and dried under reduced pressure to obtain a white powdery resin represented by the following chemical formula (XVI).

The molecular weight (Mw) of this resin was 12800, and the dispersivity (Mw/Mn) was 1.98. Also, as a result of $^{13}$C-

NMR measurement, the composition ratio (molar ratio) in the following chemical formula (XVI) was l:m:n=40:40:20. In addition, the following chemical formula (XVI) is not to show a block copolymer, but to show the ratio of each constituent unit.

[Chem. 41]

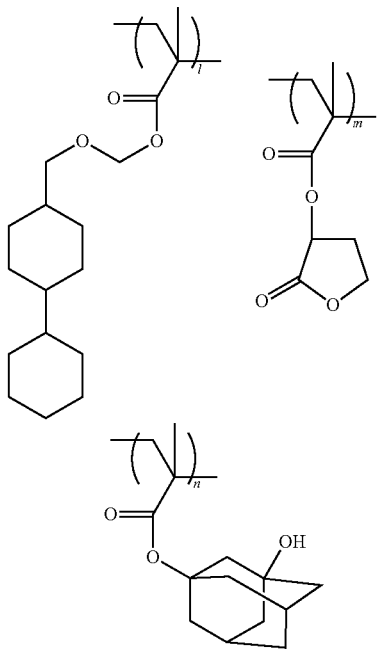

Synthesis Comparative Example 1G

A resin represented by the following chemical formula (XVII) was obtained by synthesizing similarly to Synthesis Example 1G, except that BCHMMM was substituted with 2-methyl-2-adamantyl methacrylate. The molecular weight (Mw) of this resin was 13500, and the dispersivity (Mw/Mn) was 2.30.

[Chem. 42]

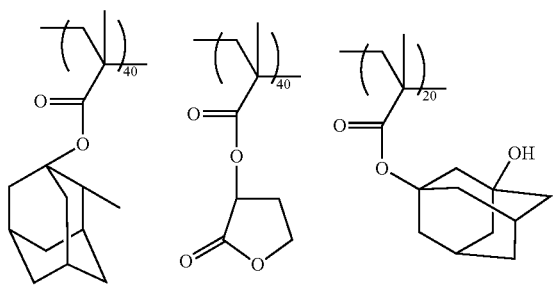

Synthesis Comparative Example 2G

A resin represented by the following chemical formula (XVIII) was obtained by synthesizing similarly to Synthesis Example 1G, except that BCHMMM was substituted with TCDMMM. The molecular weight (Mw) of this resin was 12400, and the dispersivity (Mw/Mn) was 1.96.

In addition, TCDMMM was synthesized according to the method described in International Patent Application No. PCT/JP2008/71894.

[Chem. 43]

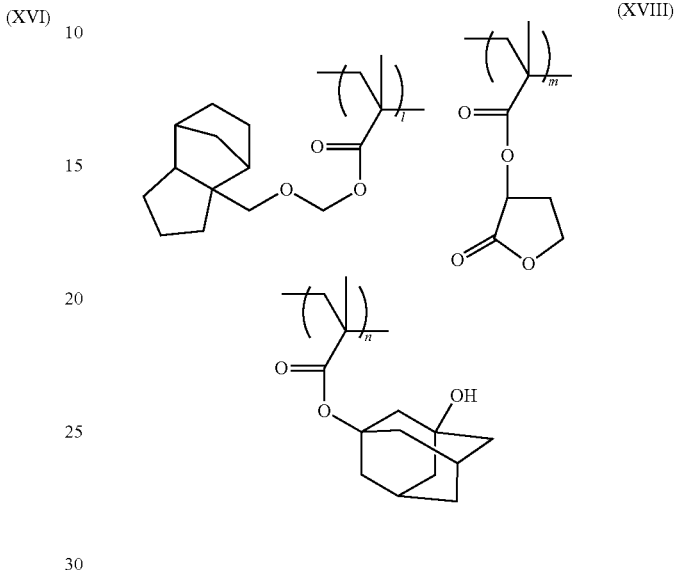

Example 1G

A resin solution was applied onto a silicon wafer and baked at 110 to 130° C. for 60 seconds to form a photoresist layer with a film thickness of 100 nm. Here, the resin solution was prepared by compounding a compound of the above chemical formula (XVI): 1 part, triphenylsulfonium nonafluoromethanesulfonate: 1 part, tributylamine: 0.1 part, and PGMEA: 92 parts.

Next, by exposing with an electron beam drawing equipment (made by ELIONIX; ELS-7500, 50 keV), baking (PEB) at 115° C. for 90 seconds, and developing with a 2.38% by mass tetramethylammonium hydroxide (TMAH) aqueous solution for 60 seconds, a positive type pattern was obtained. The result is shown in Table 3.

Comparative Example 1G

A resin solution was prepared similarly to Example 1G, except that the compound of chemical formula (XVI) in the resin solution was substituted with a compound of chemical formula (XVII), to form a photoresist layer. By developing similarly to Example 1G, a positive type pattern was obtained. The result is shown in Table 3.

Comparative Example 2G

A resin solution was prepared similarly to Example 1G, except that the compound of chemical formula (XVI) in the resin solution was substituted with a compound of chemical formula (XVIII), to form a photoresist layer. By developing similarly to Example 1G, a positive type pattern was obtained. The result is shown in Table 3.

Examples 2G to 6G

A compound solution was applied onto a silicon wafer and baked at 130° C. for 60 seconds to form a photoresist layer with a film thickness of 50 nm. Here, the compound solution was each prepared by compounding the above BCHP-CR-1, BCHP-CR-2, BCH50-CR-3, BCH50-CR-4 or a compound of chemical formula (XV): 5 parts, triphenylsulfonium nonafluoromethanesulfonate: 1.5 parts, trioctylamine: 0.15 part, and PGME: 93.35 parts.

Next, by exposing with an electron beam drawing equipment (made by ELIONIX; ELS-7500, 50 keV), baking (PEB) at 100° C. for 90 seconds, and developing with a 2.38% by mass tetramethylammonium hydroxide (TMAH) aqueous solution for 60 seconds, a positive type pattern was obtained. The result is shown in Table 3.

TABLE 3

| | Resin/Compound | Resolution | Sensitivity |
|---|---|---|---|
| Example 1G | Resin (XVI) | 40 nmL/S | 12 µC/cm² |
| Comparative Example 1G | Resin (XVII) | 80 nmL/S | 26 µC/cm² |
| Comparative Example 2G | Resin (XVIII) | 50 nmL/S | 15 µC/cm² |
| Example 2G | BCHP-CR-1 | 35 nmL/S | 20 µC/cm² |
| Example 3G | BCHP-CR-2 | 35 nmL/S | 15 µC/cm² |
| Example 4G | BCH50-CR-3 | 35 nmL/S | 15 µC/cm² |
| Example 5G | BCH50-CR-4 | 35 nmL/S | 20 µC/cm² |
| Example 6G | Compound (XV) | 35 nmL/S | 15 µC/cm² |

INDUSTRIAL APPLICABILITY

According to the invention, (1) (monohalogen substituted methyl)(bicyclohexyl group-containing alkyl)ethers as a novel bicyclohexane derivative compound useful as a modifier and a dry etching resistance improver of a photoresist resin in the photolithography field, an intermediate of drugs and pesticides, other various industrial products and the like, and a manufacturing method of the same, (2) a bicyclohexane derivative compound useful as an optical material such as a crosslinkable resin, an optical fiber, an optical waveguide, an optical disk substrate and a photoresist, and raw material thereof, an intermediate of drugs and pesticides, other various industrial products, and the like, and (3) a resin and/or a compound, a composition, and a raw material compound thereof, all excellent in alkali developability and substrate adhesion, which can achieve improvement in the resolution and the line edge roughness without deteriorating the basic physical property of a resist such as pattern shape, dry etching resistance and heat resistance, as a chemical amplification type resist sensitive to far-ultraviolet represented by a KrF excimer laser, an ArF excimer laser, an F2 excimer laser or EUV, can be provided.

What is claimed is:

1. A bicyclohexane derivative compound of formula (II)

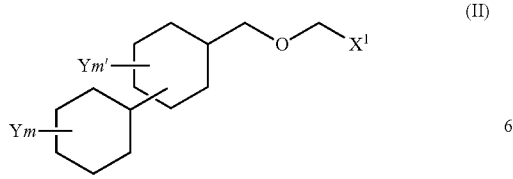

(II)

wherein Y independently represents a halogen atom, an acyloxy group, an alkoxycarbonyl group or a hydroxyl group, $X^1$ represents a halogen atom, m represents an integer of 0 to 11, and m' represents an integer of 0 to 10.

2. A bicyclohexane derivative compound of formula (VI)

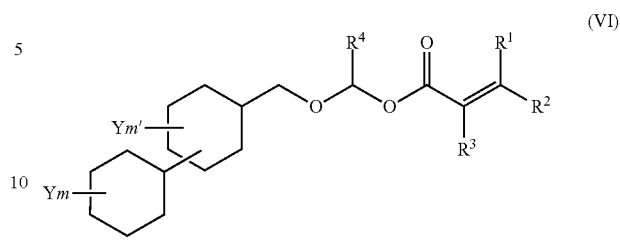

(VI)

wherein Y independently represents a halogen atom, an acyloxy group, an alkoxycarbonyl group or a hydroxyl group, m represents an integer of 0 to 11, and m' represents an integer of 0 to 10, and $R^1$ to $R^4$ each independently represents a hydrogen atom or an alkyl group of 1 to 3 carbons.

3. A bicyclohexane derivative compound according to claim 2, wherein general formula (VI) is the following general formula (VIII) or (IX)

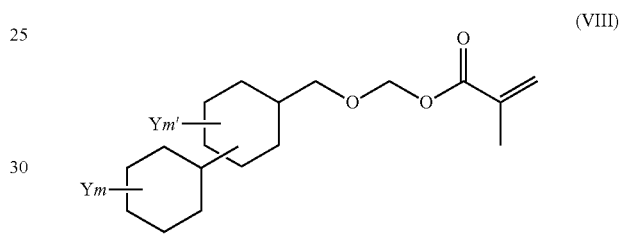

(VIII)

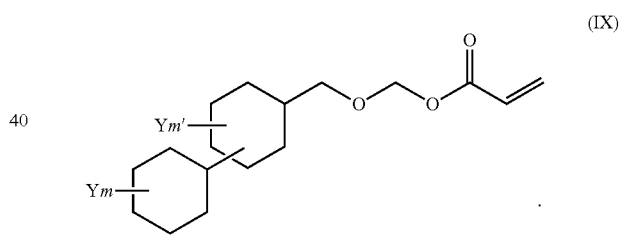

(IX)

4. A bicyclohexane derivative compound of formula (III)

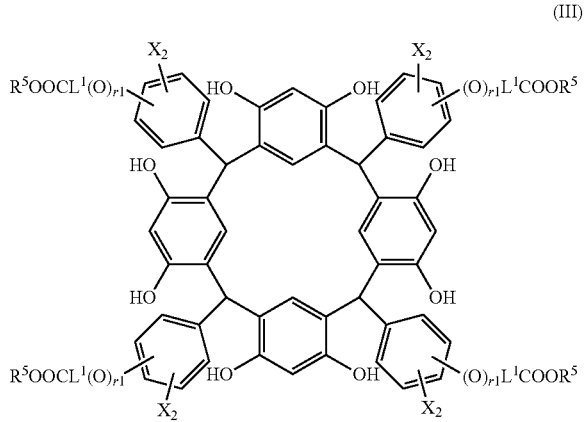

(III)

wherein $R^5$ is an acid dissociative functional group represented by the following general formula (V), $X^2$ is a hydrogen atom or a halogen atom, $L^1$ is a divalent organic group selected from a single bond, or a linear or branched alkylene group of 1 to 4 carbons, and $r^1$ is 0 or 1

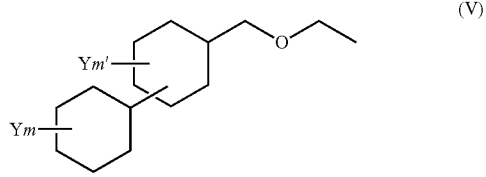

(V)

, wherein Y independently represents an alkyl group of 1 to 10 carbons, a halogen atom, an acyloxy group, an alkoxycarbonyl group or a hydroxyl group, m represents an integer of 0 to 11, and m' represents an integer of 0 to 10.

5. A bicyclohexane derivative compound of formula (III-2)

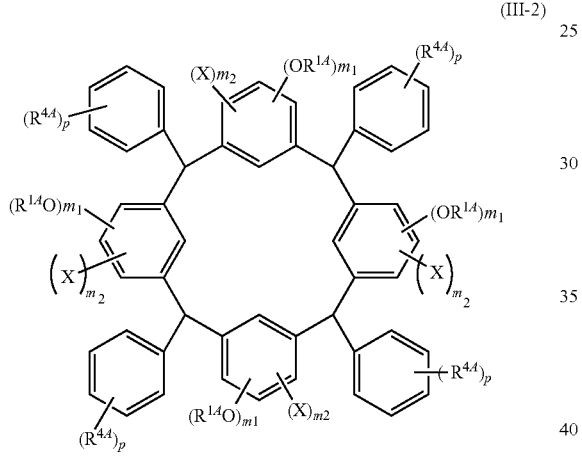

(III-2)

wherein $R^{1A}$ is an acid dissociative functional group represented by the following general formula (V) or a hydrogen atom, at least one of $R^{1A}$ is an acid dissociative functional group represented by the following general formula (V), $R^{4A}$ is a functional group selected from the group consisting of an alkyl group of 1 to 20 carbons, a cycloalkyl group of 3 to 20 carbons, an aryl group of 6 to 20 carbons, an alkoxy group of 1 to 20 carbons, a cyano group, a nitro group, a heterocyclic group, a hydroxyl group, a halogen atom, a carboxyl group and an alkylsilyl group of 1 to 20 carbons, or an acid dissociative functional group selected from the group consisting of a substituted methoxy group of 2 to 20 carbons, a 1-substituted ethoxy group of 3 to 20 carbons, a 1-substituted-n-propoxy group of 4 to 20 carbons, a 1-branched alkyloxy group of 3 to 20 carbons, a silyloxy group of 1 to 20 carbons, an acyloxy group of 2 to 20 carbons, a 1-substituted alkoxyalkyloxy group of 2 to 20 carbons, a cyclic etheroxy group of 2 to 20 carbons, an alkoxycarbonyloxy group of 2 to 20 carbons, an alkoxycarbonylalkyloxy group and a group represented by the following general formula (V-2), X is a hydrogen atom or a halogen atom, $m_1$ is an integer of 1 to 4, p is an integer of 0 to 5, m2 is an integer of 0 to 3, and $m_1+m_2=4$,

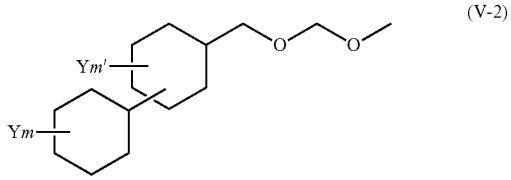

(V-2)

wherein Y independently represents an alkyl group of 1 to 10 carbons, a halogen atom, an acyloxy group, an alkoxycarbonyl group or a hydroxyl group, m represents an integer of 0 to 11, and m' represents an integer of 0 to 10, and

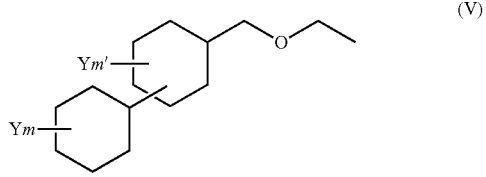

(V)

wherein Y of general formula (V) independently represents an alkyl group of 1 to 10 carbons, a halogen atom, an acyloxy group, an alkoxycarbonyl group or a hydroxyl group, m of general formula (V) represents an integer of 0 to 11, and m' of general formula (V) represents an integer of 0 to 10.

6. A bicyclohexane derivative compound of formula (IV)

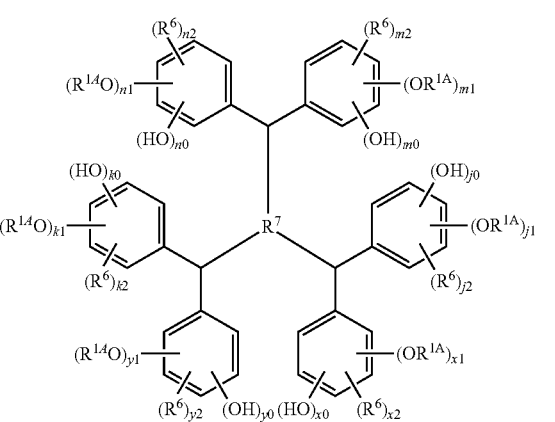

(IV)

, wherein $R^{1A}$ is an acid dissociative functional group represented by the following general formula (V) or a hydrogen atom, at least one of $R^{1A}$ is an acid dissociative functional group represented by the following general formula (V), $R^6$ represents a substituent group selected from the group consisting of a halogen atom, an alkyl group, a cycloalkyl group, an aryl group, an aralkyl group, an alkoxy group, an aryloxy group, an alkenyl group, an acyl group, an alkoxycarbonyl group, an alkyloyloxy group, an aryloyloxy group, a cyano group, and a nitro group;

$R^7$ represents a trivalent substituent group of 6 to 12 carbons having a benzene structure;

k0, j0, m0, n0, x0 and y0 are integers of 0 to 3;
k1, j1, m1, n1, x1 and y1 are integers of 0 to 3;
k2, j2, m2, n2, x2 and y2 are integers of 0 to 4; and
conditions of $1 \le k0+k1+k2 \le 5$, $1 \le j0+j1+j2 \le 5$, $1 \le m0+m1+m2 \le 5$, $1 \le n0+n1+n2 \le 5$, $1 \le x0+x1+x2 \le 5$, $1 \le y0+y1+$ y2≤5, 1≤k1+j1+m1+n1+x1+y1≤18, 1≤k0+k1≤3, 1≤j0+j1≤3, 1≤m0+m1≤3, 1≤n0+n1≤3, 1≤x0+x1≤3 and 1≤y0+y1≤3 are met, and wherein
a plurality of $R^{14}$ and $R^6$ may each be the same or different and
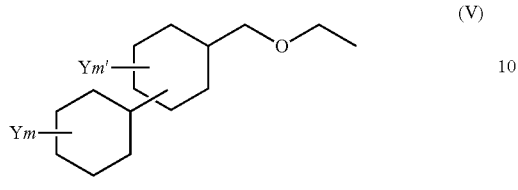
(V)
wherein Y independently represents an alkyl group of 1 to 10 carbons, a halogen atom, an acyloxy group, an alkoxycarbonyl group or a hydroxyl group, m represents an integer of 0 to 11, and m' represents an integer of 0 to 10.
* * * * *